(12) United States Patent
Garcea et al.

(10) Patent No.: US 8,039,001 B2
(45) Date of Patent: *Oct. 18, 2011

(54) THERAPEUTIC AND PROPHYLACTIC VACCINE FOR THE TREATMENT AND PREVENTION OF PAPILLOMAVIRUS INFECTION

(75) Inventors: Robert L. Garcea, Boulder, CO (US); Renee Finnen, Kinston (CA)

(73) Assignee: The Regents of the University of Colorado, a body corporate, Denver, CO (US)

( * ) Notice: Subject to any disclaimer, the term of this patent is extended or adjusted under 35 U.S.C. 154(b) by 95 days.

This patent is subject to a terminal disclaimer.

(21) Appl. No.: 12/418,481

(22) Filed: Apr. 3, 2009

(65) Prior Publication Data
US 2009/0220535 A1    Sep. 3, 2009

Related U.S. Application Data

(62) Division of application No. 10/541,895, filed as application No. PCT/US2004/00196 on Jan. 6, 2004, now Pat. No. 7,763,259.

(60) Provisional application No. 60/439,224, filed on Jan. 10, 2003.

(51) Int. Cl.
*A61K 39/12* (2006.01)

(52) U.S. Cl. .................... 424/204.1; 530/300; 435/5

(58) Field of Classification Search .................. None
See application file for complete search history.

(56) References Cited

U.S. PATENT DOCUMENTS 6,165,471 A * 12/2000 Garcea et al. .............. 424/186.1
7,670,607 B2 * 3/2010 Balloul et al. .............. 424/232.1
7,763,259 B2 * 7/2010 Garcea et al. .............. 424/204.1

OTHER PUBLICATIONS

Wakabayashi et al, Intervirology, 2002, vol. 45, pp. 300-307.*
Chen, J. Mol. Biol., 2001, vol. 307, pp. 173-182.*

* cited by examiner

*Primary Examiner* — Ali R. Salimi
(74) *Attorney, Agent, or Firm* — Faegre & Benson LLP

(57) ABSTRACT

Embodiments of the present invention provide compositions including a complexes of papillomavirus capsid polypeptide L2 and polypeptide including an immunotherapeutic epitope, and GST fusions thereof. Other embodiments also provide complexes comprising chimeras of papillomavirus L2 polypeptides non-covalently associated with papillomavirus L1 polypeptides, and GST fusions thereof. These compositions may be used to elicit immune responses in a patient to papillomavirus. Therapeutic and prophylactic vaccines for the prevention and treatment of viral infection, especially papillomavirus infection and cervical cancers and warts associated therewith, made from compositions of this invention, are also disclosed. Nucleic acids and expression vectors coding for compositions are also disclosed.

29 Claims, 7 Drawing Sheets

THE AMINO ACID SEQUENCE OF HPV 11 L2 MINOR CAPSID PROTEIN

MKPRARRRKRASATQLYQTCKATGTCPPDVIPKVEHTTIADQILKWGSLGVF
FGGLGIGTGAGSGGRAGYIPLGSSPKPAITGGPAARPPVLVEPVAPSDPSIVSLI
EESAIINAGAPEVVPPTQGGFTITSSESTTPAILDVSVTNHTTTSVFQNPLFTEPS
VIQPQPPVEASGHILISAPTITSQHVEDIPLDTFVVSSSDSGPTSSTPLPRAFPRPR
VGLYSRALQQVQVTDPAFLSTPQRLVTYDNPVYEGEDVSLQFTHESIHNAPD
EAFMDIIRLHRPAITSRRGLVRFSRIGQRGSMYTRSGQHIGARIHYFQDISPVTQ
AAEEIELHPLVAAENDTFDIYAEPFDPIPDPVQHSVTQSYLTSTPNTLSQSWGN
TTVPLSIPSDWFVQSGPDITFPTASMGTPFSPVTPALPTGPVFITGSDFYLHPTW
YFARRRRKRIPLFFTDVAA (SEQ. ID. No. 1)

FIGURE 1

THE AMINO ACID SEQUENCE OF HPV 6B L2 MINOR CAPSID PROTEIN

MAHSRARRRKRASATQLYQTCKLTGTCPPDVIPKVEHNTIADQILKWGSLGVFFGGL
GIGTGSGTGGRTGYVPLQTSAKPSITSGPMARPPVVVEPVAPSDPSIVSLIEESAIINAG
APEIVPPAHGGFTITSSETTTPAILDVSVTSHTTTSIFRNPVFTEPSVTQPQPPVEANGHI
LISAPTVTSHPIEEIPLDTFVVSSSDSGPTSSTPVPGTAPRPRVGLYSRALHQVQVTDPA
FLSTPQRLITYDNPVYEGEDVSVQFSHDSIHNAPDEAFMDIIRLHRPAIASRRGLVRYS
RIGQRGSMHTRSGKHIGARIHYFYDISPIAQAAEEIEMHPLVAAQDDTFDIYAESFEPG
INPTQHPVTNISDTYLTSTPNTVTQPWGNTTVPLSLPNDPFLQSGPDITFPTAPMGTPFS
PVTPALPTGPVFITGSGFYLHPAWYFARKRRKRIPLFFSDVAA (SEQ. ID. No. 2)

FIGURE 2

THE AMINO ACID SEQUENCE OF HPV 16 L2 MINOR CAPSID PROTEIN

MRHKRSAKRTKRASATQLYKTCKQAGTCPPDIIPKVEGKTIAEQILQYGSMGVFFGG
LGIGTGSGTGGRTGYIPLGTRPPTATDTLAPVRPPLTVDPVGPSDPSIVSLVEETSFIDA
GAPTSVPSIPPDVSGFSITTSTDTTPAILDINNTVTTVTTHNNPTFTDPSVLQPPTPAETG
GHFTLSSSTISTHNYEEIPMDTFIVSTNPNTVTSSTPIPGSRPVARLGLYSRTTQQVKVV
DPAFVTTPTKLITYDNPAYEGIDVDNTLYFSSNDNSINIAPDPDFLDIVALHRPALTSR
RTGIRYSRIGNKQTLRTRSGKSIGAKVHYYYDLSTIDPAEEIELQTITPSTYTTTSHAAS.
PTSINNGLYDIYADDFITDTSTTPVPSVPSTSLSGYIPANTTIPFGGAYNIPLVSGPDIPIN
ITDQAPSLIPIVPGSPQYTIADAGDFYLHPSYYMLRKRRKRLPYFFSDVSLAA (SEQ. ID. No. 3)

FIGURE 3

THE AMINO ACID SEQUENCE OF HPV 33 L2 MINOR CAPSID PROTEIN

MRHKRSTRRKRASATQLYQTCKATGTCPPDVIPKVEGSTIADQILKYGSLGVFFGGL
GIGTGSGSGGRTGYVPIGTDPPTAAIPLQPIRPPVTVDTVGPLDSSIVSLIEETSFIEAGA
PAPSIPTPSGFDVTTSADTTPAIINVSSVGESSIQTISTHLNPTFTEPSVLHPPAPAEASGH
FIFSSPTVSTQSYENIPMDTFVVSTDSSNVTSSTPIPGSRPVARLGLYSRNTQQVKVVD
PAFLTSPHKLITYDNPAFESFDPEDTLQFQHSDISPAPDPDFLDIIALHRPAITSRRHTVR
FSRVGQKATLKTRSGKQIGARIHYYQDLSPIVPLDHTVPNEQYELQPLHDTSTSSYSIN
DGLYDVYADDVDNVHTPMQHSYSTFATTRTSNVSIPLNTGFDTPVMSGPDIPSPLFPT
SSPFVPISPFFPFDTIVVDGADFVLHPSYFILRRRRKRFPYFFTDVRVAA (SEQ. ID. No. 4)

FIGURE 4

44 Residue L2 domain Required for L1 Binding

```
              A   AEE          A
              *   ***          *
HPV11     SGPDITFPTASMG-TPFSPVTPAL----PTGPVFITG-----SDFYLHPTWYFA-  (396-439)
HPV6b     SGPDITFPTAPMG-TPFSPVTPAL----PTGPVFITG-----SGFYLHPAWYFA-  (400-443)
HPV16     SGPDIPINITDQA-PSLIPIVPGS----PQYTIIADA-----GDFYLHPSYYML-  (412-455)
HPV33     SGPDIPSPLFPTSSPFV-PISPFF----PFDTIVVDG-----ADFVLHPSYFIL-  (406-449)
*  HPV1a  TSLHVYYPNSS---KGT-PIINPEESF-TPLVIIALNNS---TGDFELHPSL----  (455-498)
*  HPV5   KGYYVAYPESRNNAEII-VPTPDI----PVVIIHTHDN---TGDFYLHPSL----  (466-508)
*  HPV12  QGYYVAYPEHRNTAEII-NPTPDI----PVVVIHTHDN---SGDFYLHPSL----  (466-508)
*  COPV1  EGVHIIHPGSESD-FWLEPVTPDS----TPAIVIDILDS---SADYYLHPSLI---  (459-503)
** BPV1   PDTYSASPVTDPDSTS--PSLVIDDTTTPIIIDGHTVDLYSSNYTLHPSLL---  (410-460)
``` hydrophobic region between conserved prolines

FIGURE 5

```
                          SEQUENCE LISTING

<160> NUMBER OF SEQ ID NOS: 57

<210> SEQ ID NO 1
<211> LENGTH: 455
<212> TYPE: PRT
<213> ORGANISM: Human papillomavirus type 11

<400> SEQUENCE: 1

Met Lys Pro Arg Ala Arg Arg Arg Lys Arg Ala Ser Ala Thr Gln Leu
1               5                   10                  15

Tyr Gln Thr Cys Lys Ala Thr Gly Thr Cys Pro Pro Asp Val Ile Pro
            20                  25                  30

Lys Val Glu His Thr Thr Ile Ala Asp Gln Ile Leu Lys Trp Gly Ser
        35                  40                  45

Leu Gly Val Phe Phe Gly Gly Leu Gly Ile Gly Thr Gly Ala Gly Ser
    50                  55                  60

Gly Gly Arg Ala Gly Tyr Ile Pro Leu Gly Ser Ser Pro Lys Pro Ala
65                  70                  75                  80

Ile Thr Gly Gly Pro Ala Ala Arg Pro Pro Val Leu Val Glu Pro Val
                85                  90                  95

Ala Pro Ser Asp Pro Ser Ile Val Ser Leu Ile Glu Glu Ser Ala Ile
            100                 105                 110
```

```
Ile Asn Ala Gly Ala Pro Glu Val Val Pro Pro Thr Gln Gly Gly Phe
        115                 120                 125

Thr Ile Thr Ser Ser Glu Ser Thr Thr Pro Ala Ile Leu Asp Val Ser
        130                 135                 140

Val Thr Asn His Thr Thr Thr Ser Val Phe Gln Asn Pro Leu Phe Thr
145                 150                 155                 160

Glu Pro Ser Val Ile Gln Pro Gln Pro Pro Val Glu Ala Ser Gly His
                    165                 170                 175

Ile Leu Ile Ser Ala Pro Thr Ile Thr Ser Gln His Val Glu Asp Ile
                180                 185                 190

Pro Leu Asp Thr Phe Val Val Ser Ser Asp Ser Gly Pro Thr Ser
        195                 200                 205

Ser Thr Pro Leu Pro Arg Ala Phe Pro Arg Pro Arg Val Gly Leu Tyr
        210                 215                 220

Ser Arg Ala Leu Gln Gln Val Gln Val Thr Asp Pro Ala Phe Leu Ser
225                 230                 235                 240

Thr Pro Gln Arg Leu Val Thr Tyr Asp Asn Pro Val Tyr Glu Gly Glu
                    245                 250                 255

Asp Val Ser Leu Gln Phe Thr His Glu Ser Ile His Asn Ala Pro Asp
                260                 265                 270

Glu Ala Phe Met Asp Ile Ile Arg Leu His Arg Pro Ala Ile Thr Ser
            275                 280                 285

Arg Arg Gly Leu Val Arg Phe Ser Arg Ile Gly Gln Arg Gly Ser Met
        290                 295                 300

Tyr Thr Arg Ser Gly Gln His Ile Gly Ala Arg Ile His Tyr Phe Gln
305                 310                 315                 320

Asp Ile Ser Pro Val Thr Gln Ala Ala Glu Gly Ile Glu Leu His Pro
                    325                 330                 335

Leu Val Ala Ala Glu Asn Asp Thr Phe Asp Ile Tyr Ala Glu Pro Phe
                340                 345                 350

Asp Pro Ile Pro Asp Pro Val Gln His Ser Val Thr Gln Ser Tyr Leu
            355                 360                 365

Thr Ser Thr Pro Asn Thr Leu Ser Gln Ser Trp Gly Asn Thr Thr Val
        370                 375                 380

Pro Leu Ser Ile Pro Ser Asp Trp Phe Val Gln Ser Gly Pro Asp Ile
385                 390                 395                 400

Thr Phe Pro Thr Ala Ser Met Gly Thr Pro Phe Ser Pro Val Thr Pro
                    405                 410                 415

Ala Leu Pro Thr Gly Pro Val Phe Ile Thr Gly Ser Asp Phe Tyr Leu
                420                 425                 430

His Pro Thr Trp Tyr Phe Ala Arg Arg Arg Arg Lys Arg Ile Pro Leu
            435                 440                 445

Phe Phe Thr Asp Val Ala Ala
        450                 455

<210> SEQ ID NO 2
<211> LENGTH: 459
<212> TYPE: PRT
<213> ORGANISM: Human papillomavirus type 6b

<400> SEQUENCE: 2

Met Ala His Ser Arg Ala Arg Arg Arg Lys Arg Ala Ser Ala Thr Gln
1               5                   10                  15

Leu Tyr Gln Thr Cys Lys Leu Thr Gly Thr Cys Pro Pro Asp Val Ile
            20                  25                  30
```

```
Pro Lys Val Glu His Asn Thr Ile Ala Asp Gln Ile Leu Lys Trp Gly
         35                  40                  45

Ser Leu Gly Val Phe Phe Gly Leu Gly Ile Gly Thr Gly Ser Gly
 50                  55                  60

Thr Gly Gly Arg Trp Gly Thr Val Pro Leu Gln Thr Ser Ala Lys Pro
 65                  70                  75                  80

Ser Ile Thr Ser Gly Pro Met Ala Arg Pro Pro Val Val Glu Pro
                 85                  90                  95

Val Ala Pro Ser Asp Pro Ser Ile Val Ser Leu Ile Glu Glu Ser Ala
                100                 105                 110

Ile Ile Asn Ala Gly Ala Pro Glu Ile Val Pro Pro Ala His Gly Gly
         115                 120                 125

Phe Thr Ile Thr Ser Ser Glu Thr Thr Thr Pro Ala Ile Leu Asp Val
         130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Val Thr Ser His Pro Ile Glu Glu
             180                 185                 190

Ile Pro Leu Asp Thr Phe Val Val Ser Ser Ser Asp Ser Gly Pro Thr
        195                 200                 205

Ser Ser Thr Pro Val Pro Gly Thr Ala Pro Arg Pro Arg Val Gly Leu
    210                 215                 220

Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
                245                 250                 255

Glu Asp Val Ser Val Gln Phe Ser His Asp Ser Ile His Asn Ala Pro
                260                 265                 270

Asp Glu Ala Phe Met Asp Ile Ile Arg Leu His Arg Pro Ala Ile Ala
        275                 280                 285

Ser Arg Arg Gly Leu Val Arg Tyr Ser Arg Ile Gly Gln Arg Gly Ser
    290                 295                 300

Met His Thr Arg Ser Gly Lys His Ile Gly Ala Arg Ile His Tyr Phe
305                 310                 315                 320

Tyr Asp Ile Ser Pro Ile Ala Gln Ala Ala Glu Glu Ile Glu Met His
                325                 330                 335

Pro Leu Val Ala Ala Gln Asp Thr Phe Asp Ile Tyr Ala Glu Ser
        340                 345                 350

Phe Glu Pro Gly Ile Asn Pro Thr Gln His Pro Val Thr Asn Ile Ser
    355                 360                 365

Asp Thr Tyr Leu Thr Ser Thr Pro Asn Thr Val Thr Gln Pro Trp Gly
370                 375                 380

Asn Thr Thr Val Pro Leu Ser Leu Pro Asn Asp Pro Phe Leu Gln Ser
385                 390                 395                 400

Gly Pro Asp Ile Thr Phe Pro Thr Ala Pro Met Gly Thr Pro Phe Ser
                405                 410                 415

Pro Val Thr Pro Ala Leu Pro Thr Gly Pro Val Phe Ile Thr Gly Ser
            420                 425                 430

Gly Phe Tyr Leu His Pro Ala Trp Tyr Phe Ala Arg Lys Arg Arg Lys
        435                 440                 445

Arg Ile Pro Leu Phe Phe Ser Asp Val Ala Ala
```

<210> SEQ ID NO 3
<211> LENGTH: 473
<212> TYPE: PRT
<213> ORGANISM: Human papillomavirus type 16

<400> SEQUENCE: 3

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Ser Thr Thr Pro Val Pro Ser
```

-continued

```
                    370                 375                 380
Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                    405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
                    435                 440                 445

His Pro Ser Tyr Tyr Met Leu Arg Lys Arg Arg Lys Arg Leu Pro Tyr
                    450                 455                 460

Phe Phe Ser Asp Val Ser Leu Ala Ala
465                 470

<210> SEQ ID NO 4
<211> LENGTH: 467
<212> TYPE: PRT
<213> ORGANISM: Human papillomavirus type 33

<400> SEQUENCE: 4

Met Arg His Lys Arg Ser Thr Arg Arg Lys Arg Ala Ser Ala Thr Gln
1               5                   10                  15

Leu Tyr Gln Thr Cys Lys Ala Thr Gly Thr Cys Pro Pro Asp Val Ile
                20                  25                  30

Pro Lys Val Glu Gly Ser Thr Ile Ala Asp Gln Ile Leu Lys Tyr Gly
            35                  40                  45

Ser Leu Gly Val Phe Phe Gly Gly Leu Gly Ile Gly Thr Gly Ser Gly
    50                  55                  60

Ser Gly Gly Arg Thr Gly Tyr Val Pro Ile Gly Thr Asp Pro Pro Thr
65                  70                  75                  80

Ala Ala Ile Pro Leu Gln Pro Ile Arg Pro Pro Val Thr Val Asp Thr
                    85                  90                  95

Val Gly Pro Leu Asp Ser Ser Ile Val Ser Leu Ile Glu Glu Thr Ser
                100                 105                 110

Phe Ile Glu Ala Gly Ala Pro Ala Pro Ser Ile Pro Thr Pro Ser Gly
            115                 120                 125

Phe Asp Val Thr Thr Ser Ala Asp Thr Thr Pro Ala Ile Ile Asn Val
    130                 135                 140

Ser Ser Val Gly Glu Ser Ser Ile Gln Thr Ile Ser Thr His Leu Asn
145                 150                 155                 160

Pro Thr Phe Thr Glu Pro Ser Val Leu His Pro Pro Ala Pro Ala Glu
                165                 170                 175

Ala Ser Gly His Phe Ile Phe Ser Ser Pro Thr Val Ser Thr Gln Ser
                180                 185                 190

Tyr Glu Asn Ile Pro Met Asp Thr Phe Val Val Ser Thr Asp Ser Ser
            195                 200                 205

Asn Val Thr Ser Ser Thr Pro Ile Pro Gly Ser Arg Pro Val Ala Arg
    210                 215                 220

Leu Gly Leu Tyr Ser Arg Asn Thr Gln Gln Val Lys Val Val Asp Pro
225                 230                 235                 240

Ala Phe Leu Thr Ser Pro His Lys Leu Ile Thr Tyr Asp Asn Pro Ala
                245                 250                 255

Phe Glu Ser Phe Asp Pro Glu Asp Thr Leu Gln Phe Gln His Ser Asp
                260                 265                 270

Ile Ser Pro Ala Pro Asp Pro Asp Phe Leu Asp Ile Ile Ala Leu His
```

```
                275                 280                 285
Arg Pro Ala Ile Thr Ser Arg His Thr Val Arg Phe Ser Arg Val
290                 295                 300

Gly Gln Lys Ala Thr Leu Lys Thr Arg Ser Gly Lys Gln Ile Gly Ala
305                 310                 315                 320

Arg Ile His Tyr Tyr Gln Asp Leu Ser Pro Ile Val Pro Leu Asp His
                325                 330                 335

Thr Val Pro Asn Glu Gln Tyr Glu Leu Gln Pro Leu His Asp Thr Ser
            340                 345                 350

Thr Ser Ser Tyr Ser Ile Asn Asp Gly Leu Tyr Asp Val Tyr Ala Asp
        355                 360                 365

Asp Val Asp Asn Val His Thr Pro Met Gln His Ser Tyr Ser Thr Phe
    370                 375                 380

Ala Thr Thr Arg Thr Ser Asn Val Ser Ile Pro Leu Asn Thr Gly Phe
385                 390                 395                 400

Asp Thr Pro Val Met Ser Gly Pro Asp Ile Pro Ser Pro Leu Phe Pro
                405                 410                 415

Thr Ser Ser Pro Phe Val Pro Ile Ser Pro Phe Phe Pro Phe Asp Thr
            420                 425                 430

Ile Val Val Asp Gly Ala Asp Phe Val Leu His Pro Ser Tyr Phe Ile
        435                 440                 445

Leu Arg Arg Arg Arg Lys Arg Phe Pro Tyr Phe Phe Thr Asp Val Arg
    450                 455                 460

Val Ala Ala
465

<210> SEQ ID NO 5
<211> LENGTH: 34
<212> TYPE: DNA
<213> ORGANISM: Human papillomavirus type 11

<400> SEQUENCE: 5
gccgcgaagc ttcatatgtg gcggcctagc gcag                              34

<210> SEQ ID NO 6
<211> LENGTH: 38
<212> TYPE: DNA
<213> ORGANISM: Human papillomavirus type 10

<400> SEQUENCE: 6
gggcctggat ccagatctca caacacacac tgacacac                          38

<210> SEQ ID NO 7
<211> LENGTH: 38
<212> TYPE: DNA
<213> ORGANISM: Human papillomavirus type 11

<400> SEQUENCE: 7
gggcctggat ccagatctca caacacacac tgacacac                          38

<210> SEQ ID NO 8
<211> LENGTH: 28
<212> TYPE: DNA
<213> ORGANISM: Human papillomavirus type 11

<400> SEQUENCE: 8
ggggcggccg cctaggccgc cacatctg                                     28

<210> SEQ ID NO 9
```

```
<211> LENGTH: 23
<212> TYPE: DNA
<213> ORGANISM: Human papillomavirus type 11

<400> SEQUENCE: 9
gggctggcaa gccacgtttg gtc                                              23

<210> SEQ ID NO 10
<211> LENGTH: 29
<212> TYPE: DNA
<213> ORGANISM: Human papillomavirus type 11

<400> SEQUENCE: 10
aattccagat ctatacactc cgctatcgc                                        29

<210> SEQ ID NO 11
<211> LENGTH: 27
<212> TYPE: DNA
<213> ORGANISM: Human papillomavirus type 11

<400> SEQUENCE: 11
gggggatcca tgaaacctag ggcacgc                                          27

<210> SEQ ID NO 12
<211> LENGTH: 30
<212> TYPE: DNA
<213> ORGANISM: Human papillomavirus type 11

<400> SEQUENCE: 12
gggcggccgc attttgaaac acactagtgg                                       30

<210> SEQ ID NO 13
<211> LENGTH: 27
<212> TYPE: DNA
<213> ORGANISM: Human papillomavirus type 11

<400> SEQUENCE: 13
gggggatcca tgaaacctag ggcacgc                                          27

<210> SEQ ID NO 14
<211> LENGTH: 30
<212> TYPE: DNA
<213> ORGANISM: Human papillomavirus type 11

<400> SEQUENCE: 14
ggggcggcgg ctccactgcg tgtgtacatg                                       30

<210> SEQ ID NO 15
<211> LENGTH: 27
<212> TYPE: DNA
<213> ORGANISM: Human papillomavirus type 11

<400> SEQUENCE: 15
gggggatccc ccctgtttac agaaccg                                          27

<210> SEQ ID NO 16
<211> LENGTH: 30
<212> TYPE: DNA
<213> ORGANISM: Human papillomavirus type 11

<400> SEQUENCE: 16
ggggcggcgg ctccactgcg tgtgtacatg                                       30

<210> SEQ ID NO 17
```

```
<211> LENGTH: 27
<212> TYPE: DNA
<213> ORGANISM: Human papillomavirus type 11

<400> SEQUENCE: 17
gggggatccc ccctgtttac agaaccg                                               27

<210> SEQ ID NO 18
<211> LENGTH: 28
<212> TYPE: DNA
<213> ORGANISM: Human papillomavirus type 11

<400> SEQUENCE: 18
ggggcggccg cctaggccgc cacatctg                                              28

<210> SEQ ID NO 19
<211> LENGTH: 27
<212> TYPE: DNA
<213> ORGANISM: Human papillomavirus type 11

<400> SEQUENCE: 19
caaggatccg gtgcccgcat acattat                                               27

<210> SEQ ID NO 20
<211> LENGTH: 28
<212> TYPE: DNA
<213> ORGANISM: Human papillomavirus type 11

<400> SEQUENCE: 20
ggggcggccg cctaggccgc cacatctg                                              28

<210> SEQ ID NO 21
<211> LENGTH: 27
<212> TYPE: DNA
<213> ORGANISM: Human papillomavirus type 11

<400> SEQUENCE: 21
caaggatccg gtgcccgcat acattat                                               27

<210> SEQ ID NO 22
<211> LENGTH: 29
<212> TYPE: DNA
<213> ORGANISM: Human papillomavirus type 11

<400> SEQUENCE: 22
aattccgcgg ccgctatgtc aggcccaga                                             29

<210> SEQ ID NO 23
<211> LENGTH: 27
<212> TYPE: DNA
<213> ORGANISM: Human papillomavirus type 11

<400> SEQUENCE: 23
aattccggat ccgatattta tgctgaa                                               27

<210> SEQ ID NO 24
<211> LENGTH: 28
<212> TYPE: DNA
<213> ORGANISM: Human papillomavirus type 11

<400> SEQUENCE: 24
ggggcggccg cctaggccgc cacatctg                                              28

<210> SEQ ID NO 25
```

```
<211> LENGTH: 27
<212> TYPE: DNA
<213> ORGANISM: Human papillomavirus type 11

<400> SEQUENCE: 25
aattccggat cctctgggcc tgacata                                              27

<210> SEQ ID NO 26
<211> LENGTH: 28
<212> TYPE: DNA
<213> ORGANISM: Human papillomavirus type 10

<400> SEQUENCE: 26
ggggcggccg cctaggccgc cacatctg                                             28

<210> SEQ ID NO 27
<211> LENGTH: 27
<212> TYPE: DNA
<213> ORGANISM: Human papillomavirus type 11

<400> SEQUENCE: 27
aattccggat ccgatattta tgctgaa                                              27

<210> SEQ ID NO 28
<211> LENGTH: 31
<212> TYPE: DNA
<213> ORGANISM: Human papillomavirus type 11

<400> SEQUENCE: 28
aattccgcgg ccgctgcaaa gtaccatgag g                                         31

<210> SEQ ID NO 29
<211> LENGTH: 27
<212> TYPE: DNA
<213> ORGANISM: Human papillomavirus type 11

<400> SEQUENCE: 29
aattccggat cctctgggcc tgacata                                              27

<210> SEQ ID NO 30
<211> LENGTH: 31
<212> TYPE: DNA
<213> ORGANISM: Human papillomavirus type 11

<400> SEQUENCE: 30
aattccgcgg ccgctgcaaa gtaccatgag g                                         31

<210> SEQ ID NO 31
<211> LENGTH: 28
<212> TYPE: DNA
<213> ORGANISM: Human papillomavirus type 11

<400> SEQUENCE: 31
ctgtaactcc tgaagaacct acaggccc                                             28

<210> SEQ ID NO 32
<211> LENGTH: 28
<212> TYPE: DNA
<213> ORGANISM: Human papillomavirus type 11

<400> SEQUENCE: 32
gggcctgtag gttcttcagg agttacag                                             28

<210> SEQ ID NO 33
```

```
<211> LENGTH: 28
<212> TYPE: DNA
<213> ORGANISM: Human papillomavirus type 11

<400> SEQUENCE: 33
ctgtaactcc tgaattacct acaggccc                                              28

<210> SEQ ID NO 34
<211> LENGTH: 28
<212> TYPE: DNA
<213> ORGANISM: Human papillomavirus type 11

<400> SEQUENCE: 34
gggcctgtag gtaattcagg agttacag                                              28

<210> SEQ ID NO 35
<211> LENGTH: 28
<212> TYPE: DNA
<213> ORGANISM: Human papillomavirus type 11

<400> SEQUENCE: 35
ctgtaactcc tgctgaacct acaggccc                                              28

<210> SEQ ID NO 36
<211> LENGTH: 28
<212> TYPE: DNA
<213> ORGANISM: Human papillomavirus type 11

<400> SEQUENCE: 36
gggcctgtag gttcagcagg agttacag                                              28

<210> SEQ ID NO 37
<211> LENGTH: 25
<212> TYPE: DNA
<213> ORGANISM: Human papillomavirus type 11

<400> SEQUENCE: 37
acacccttta gtgctgtaac tcctg                                                 25

<210> SEQ ID NO 38
<211> LENGTH: 25
<212> TYPE: DNA
<213> ORGANISM: Human papillomavirus type 11

<400> SEQUENCE: 38
caggagttac agcactaaag ggtgt                                                 25

<210> SEQ ID NO 39
<211> LENGTH: 25
<212> TYPE: DNA
<213> ORGANISM: Human papillomavirus type 11

<400> SEQUENCE: 39
gtaggtaaag cagcagttac aggac                                                 25

<210> SEQ ID NO 40
<211> LENGTH: 25
<212> TYPE: DNA
<213> ORGANISM: Human papillomavirus type 11

<400> SEQUENCE: 40
actcctgctt tagctacagg ccctg                                                 25

<210> SEQ ID NO 41
```

```
<211> LENGTH: 25
<212> TYPE: DNA
<213> ORGANISM: Human papillomavirus type 11

<400> SEQUENCE: 41
cagggcctgt agctaaagca ggagt                                    25

<210> SEQ ID NO 42
<211> LENGTH: 35
<212> TYPE: DNA
<213> ORGANISM: Human papillomavirus type 6b

<400> SEQUENCE: 42
aattccggat ccggggcccg cattcattat tttta                         35

<210> SEQ ID NO 43
<211> LENGTH: 31
<212> TYPE: DNA
<213> ORGANISM: Human papillomavirus type 6b

<400> SEQUENCE: 43
aattccgcgg ccgcctaggc cgccacatct g                             31

<210> SEQ ID NO 44
<211> LENGTH: 35
<212> TYPE: DNA
<213> ORGANISM: Human papillomavirus type 16

<400> SEQUENCE: 44
aattccggat ccggtgctaa ggtacattat tatta                         35

<210> SEQ ID NO 45
<211> LENGTH: 32
<212> TYPE: DNA
<213> ORGANISM: Human papillomavirus type 16

<400> SEQUENCE: 45
aattccgcgg ccgcctaggc agccaaagag ac                            32

<210> SEQ ID NO 46
<211> LENGTH: 34
<212> TYPE: DNA
<213> ORGANISM: Human papillomavirus type 33

<400> SEQUENCE: 46
aattccggat ccggagctag aatacattat tatc                          34

<210> SEQ ID NO 47
<211> LENGTH: 32
<212> TYPE: DNA
<213> ORGANISM: Human papillomavirus type 33

<400> SEQUENCE: 47
aattccgcgg ccgcctaggc cgccacacgg ac                            32

<210> SEQ ID NO 48
<211> LENGTH: 33
<212> TYPE: DNA
<213> ORGANISM: Human papillomavirus type 1a

<400> SEQUENCE: 48
aattccggat ccgggccaca aagccatttt tac                           33

<210> SEQ ID NO 49
```

```
<211> LENGTH: 35
<212> TYPE: DNA
<213> ORGANISM: Human papillomavirus type 1a

<400> SEQUENCE: 49
aattccgcgg ccgcttaaaa aaaaaaatgt ttgcg                              35

<210> SEQ ID NO 50
<211> LENGTH: 32
<212> TYPE: DNA
<213> ORGANISM: Human papillomavirus type 5

<400> SEQUENCE: 50
aatccggatc cgggtcgcaa gtccattttt ac                                 32

<210> SEQ ID NO 51
<211> LENGTH: 30
<212> TYPE: DNA
<213> ORGANISM: Human papillomavirus type 5

<400> SEQUENCE: 51
aattccgcgg ccgctcacaa atattttctt                                    30

<210> SEQ ID NO 52
<211> LENGTH: 35
<212> TYPE: DNA
<213> ORGANISM: Human papillomavirus type 12

<400> SEQUENCE: 52
aattccggat ccggatcaca ggttcatttt tatag                              35

<210> SEQ ID NO 53
<211> LENGTH: 30
<212> TYPE: DNA
<213> ORGANISM: Human papillomavirus type 12

<400> SEQUENCE: 53
aattccgcgg ccgctcacaa atattttctt                                    30

<210> SEQ ID NO 54
<211> LENGTH: 33
<212> TYPE: DNA
<213> ORGANISM: Human papillomavirus type 1

<400> SEQUENCE: 54
aattccggat ccgggccaca aagccatttt tac                                33

<210> SEQ ID NO 55
<211> LENGTH: 35
<212> TYPE: DNA
<213> ORGANISM: Human papillomavirus type 1

<400> SEQUENCE: 55
aattccgcgg ccgcttaaaa aaaaaaatgt ttgcg                              35

<210> SEQ ID NO 56
<211> LENGTH: 33
<212> TYPE: DNA
<213> ORGANISM: Human papillomavirus type 1

<400> SEQUENCE: 56
aattccggat ccggaccaca gctacatgtc agg                                33

<210> SEQ ID NO 57
```

```
<211> LENGTH: 34
<212> TYPE: DNA
<213> ORGANISM: Human papillomavirus type 1

<400> SEQUENCE: 57
ctcgagttag gcatgtttcc gttttttcg tttc                                    34
```

THERAPEUTIC AND PROPHYLACTIC VACCINE FOR THE TREATMENT AND PREVENTION OF PAPILLOMAVIRUS INFECTION

CROSS-REFERENCE TO OTHER APPLICATIONS

This application claims priority under 35 U.S.C. 121 as a divisional application of U.S. patent application Ser. No. 10/541,895, filed Feb. 16, 2006 entitled, "Therapeutic and Prophylactic Vaccine for the Treatment and Prevention of Papillomavirus Infection," now Issued U.S. Pat. No. 7,763,259, issued on Jul. 27, 2010, which claims the benefit of PCT/US04/00196, filed Jan. 6, 2004, which claims priority to U.S. Provisional Application Ser. No. 60/439,224 filed on Jan. 10, 2003, all of which are incorporated herein by reference in their entirety.

BACKGROUND OF THE INVENTION

1. Field of the Invention

The present invention provides novel vaccines and diagnostic agents for the prevention, treatment and/or diagnosis of viral infection, especially papillomavirus infection and cervical cancers associated therewith. More specifically, the present invention provides an efficient method for incorporating immunotherapeutic proteins into capsomeres, which may then be used to elicit immune responses.

2. Description of the Prior Art

Papillomaviruses infect a wide variety of different species of animals including humans. Infection is typically characterized by the induction of benign epithelial and fibro-epithelial tumors, or warts at the site of infection. Each species of vertebrate is infected by a species-specific set of papillomavirus, itself comprising several different papillomavirus types. For example, more than sixty different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses cause genital warts, a prevalent sexually-transmitted disease. HPV types 6 and 11 are most commonly associated with benign genital warts condylomata acuminata. Genital warts are very common, and subclinical or inapparent HPV infection is even more common than clinical infection. While most HPV-induced lesions are benign, lesions arising from certain papillomavirus types e.g., HPV-16 and HPV-18, can undergo malignant progression. Moreover, infection by one of the malignancy-associated papillomavirus types is considered to be a significant risk factor in the development of cervical cancer, the second most common cancer in women worldwide. Of the HPV genotypes involved in cervical cancer, HPV-16 is the most common, being found in about 50% of cervical cancers. The prevalence of HPV-18 ranges from approximately 8-31% depending on the geographical location, and in most areas worldwide, HPV-45 is the third most frequent, oncogenic HPV type (Bosch, F. X., et al., J Natl. Cancer Inst., 87:796-802 (1995).

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2).

Yuan, et al., J Virology, 75:7848-53 (2001), describe the preparation of canine oral papillomavirus capsid L1 protein-glutathione-S-transferase fusion proteins and their expression in E. coli. This publication demonstrates the efficacy of non-VLP vaccines in the dog canine oral papillomavirus (COPV) model. COPV is the model previously used to validate VLP vaccines. Here, GST-L1 fusions were expressed in E. coli, and, although in capsomere form, had not been assembled into VLPs before use as a vaccine. The paper demonstrated that GST-L1 fusions retained their native conformations and further, completely protected dogs from viral infection with COPV. The authors conclude that VLPs are not necessary for efficacy of capsid protein L1 vaccines against papillomavirus, and that GST fusion proteins, which may be purified efficiently and economically in bacteria, are effective to protect dogs against COPV.

U.S. Pat. No. 6,165,471, issued Dec. 26, 2000 to Robert L. Garcea, et al., also discloses non-VLP vaccines composed of capsomeres of HPV L1 with carboxy-terminal deletions and mutations of specific cysteine residues which inhibit the formation of VLPs. These capsomeres were produced in bacterial expression systems, and they were efficacious in eliciting HPV neutralizing antibodies in rabbits. This reference is incorporated herein by reference in its entirety.

PCT/US01/18702 entitled "Stable (Fixed) Forms Of Viral Capsid Proteins, And Viral Capsid Protein Fusions, Preferably Papillomavirus L1 Proteins, And Uses Thereof," describes papillomavirus capsid protein L1 or L2 proteins expressed as glutathione-S-transferase fusion proteins in bacteria. These fusions expressed in E. coli retain L1 native conformation and immunogenic activity as measured by assays with neutralizing antibodies. This reference is incorporated herein by reference in its entirety.

Prophylactic vaccines currently in clinical trials are based upon VLPs (virus like particles) assembled from HPV16 L1. See, Cain, J. M., et al., Science, 288:1753-55 (2000); Gissmann, L., et al., Intervirology, 44:167-75 (2001); Harro, et al., J. Natl Cancer Inst, 93:284-292 (2001); Schiller, J. T., et al., J Clin Virol, 19:67-74 (2000); and Schiller, J. T., et al., Expert Opin Biol Ther, 1:571-81. However, these types of vaccines are relatively expensive to produce in that they require eukaryotic expression systems or complex purification, and are less stable than capsomere preparations.

Additionally, VLP vaccines have the shortcoming that they may not provide cross protection against other papillomavirus serotypes, as neutralizing immune responses tend to be predominately type-specific. See Christensen, et al., J Gen Virol, 75 (Pt 9):2271-76 (1994); Christensen, et al., Virology, 175:1-9 (1990); Roden, et al., J Virol, 70:5875-83 (1996); Roden, et al., J Virol, 70:3298-301 (1996); Rose, et al., J Gen Virol, 75 (Pt 9):2445-49 (1994); and White, et al., J Virol, 73:4882-9 (1999).

Papillomavirus capsid protein L2 has been shown to generate cross-neutralizing antisera. See Roden, "Minor capsid protein of human genital papillomaviruses contains subdominant, cross-neutralizing epitopes," Virology, 270:254-7 (2000).

A further drawback to approaches that do not incorporate papillomavirus capsid protein L2 into capsomeres of papillomavirus capsid protein L1 is that requirements for L1 capsomers to assemble into VLPs are somewhat strict, i.e. acidic pH, such as pH 5.2, is required for assembly. Thus, if it is desired to produce VLPs, it is desirable to produce capsomeres that assemble more readily into VLPs, i.e. at more physiological pH.

Currently, one approach to developing a therapeutic vaccine for treating established cervical carcinomas has been to create VLPs using papillomavirus capsid protein L1 also containing an immunotherapeutic protein, typically E7. See Miller, et al., Virology, 234:93-111. However, this approach does not include papillomavirus capsid protein L2, which can broaden the therapeutic usefulness of such a vaccine. Another drawback to this approach is that smaller amounts of immunotherapeutic protein can be incorporated into VLPs using this approach, certainly much less than one therapeutic protein per capsomere.

Thus, there remains a need in the art to produce papillomavirus vaccines containing both L1 and L2 viral capsid proteins to potentially generate a broader spectrum of protection against different papillomavirus serotypes. Additionally, there remains a need in the art to produce a therapeutic vaccine in order to treat established cervical cancer which represents an improvement over current therapeutic vaccines. There remains a need for such compositions to be produced economically, preferably from bacterial expression systems. Further, there is a need in the art to for bacterially produced papillomavirus capsomeres that assemble into VLPs at physiologic pH.

SUMMARY OF THE INVENTION

This invention provides chimeric compositions comprising a papillomavirus capsid polypeptide L2 or portions thereof, a polypeptide including but not limited to an immunotherapeutic epitope, and glutathione S transferase (GST) fusions thereof. The present invention also provides complexes comprising a papillomavirus capsid polypeptide L2 or portions thereof, a polypeptide including but not limited to an immunotherapeutic epitope, and glutathione S transferase (GST) fusions thereof non-covalently associated with papillomavirus L1 polypeptides. These compositions may be used to elicit immune responses in a patient to papillomavirus. Therapeutic and prophylactic vaccines for the prevention and treatment of viral infection, especially papillomavirus infection and cervical cancers and warts associated therewith, made from compositions of this invention, are also disclosed. Nucleic acids and expression vectors coding for compositions of this invention are also disclosed.

More specifically, the chimeric compositions of the present invention comprise a papillomavirus capsid protein L2 polypeptide, which includes a papillomavirus capsid protein L1 binding region, fused with a polypeptide having an immunogenic epitope at the amino or carboxy terminal end, preferably expressed as a GST fusion protein. It is further desirable to provide these chimeras from a bacterial expression system for economical production.

The present invention further contemplates providing a complex containing chimeric proteins of the present invention non-covalently associated with papillomavirus capsid protein L1 proteins. These complexes may be provided as capsomeres with a stoichiometry of 1 chimeric protein to 5 papillomavirus capsid L1 polypeptides. Alternatively these complexes may provide immunogenic epitopes at a stoichiometry of 1 to 5 papillomavirus capsid L1 proteins.

The present invention further discloses VLPs, which are capable of forming at physiological pH, have capsomeres that are capable of potentially incorporating seventy two copies of a chimeric protein of the present invention.

The present invention further provides capsomere vaccine formulations having an intact structural papilloma viral protein L1 expressed as a fusion protein with additional amino acid residues from a second protein. Preferred capsomeres are made up entirely of L1 fusion proteins, the sequence of L1 is well known in the art and can be found in U.S. Pat. No. 6,228,368 which is incorporated herein in its entirety. Amino acids of the second protein can be derived from numerous sources (including amino acid residues from the first protein). Preferably, the two fusion proteins are linked together by a linker of one or more amino acids in length.

BRIEF DESCRIPTION OF THE FIGURES

The accompanying drawings, which are incorporated in and form a part of the specifications, illustrate the preferred embodiments of the present invention, and together with the description serve to explain the principles of the invention.
In the Drawings:

FIG. 1 shows the amino acid sequence of a DNA encoding a peptide of L2 of an HPV 11 L2 papilloma virus (SEQ ID NO: 1).

FIG. 2 shows the amino acid sequence of a DNA encoding a peptide of L2 of an HPV 6B L2 papilloma virus (SEQ ID NO:2).

FIG. 3 shows the amino acid sequence of a DNA encoding a peptide of L2 of an HPV 16 L2 papilloma virus (SEQ ID NO:3).

FIG. 4 shows the amino acid sequence of a DNA encoding a peptide of L2 of an HPV 33 L2 papilloma virus (SEQ ID NO:4).

FIG. 5 is a schematic representing the 44 residues L2 domain required for L1 binding, and highlighting the hydrophobic region between conserved prolines.

DETAILED DESCRIPTION OF THE INVENTION

Figure 6:
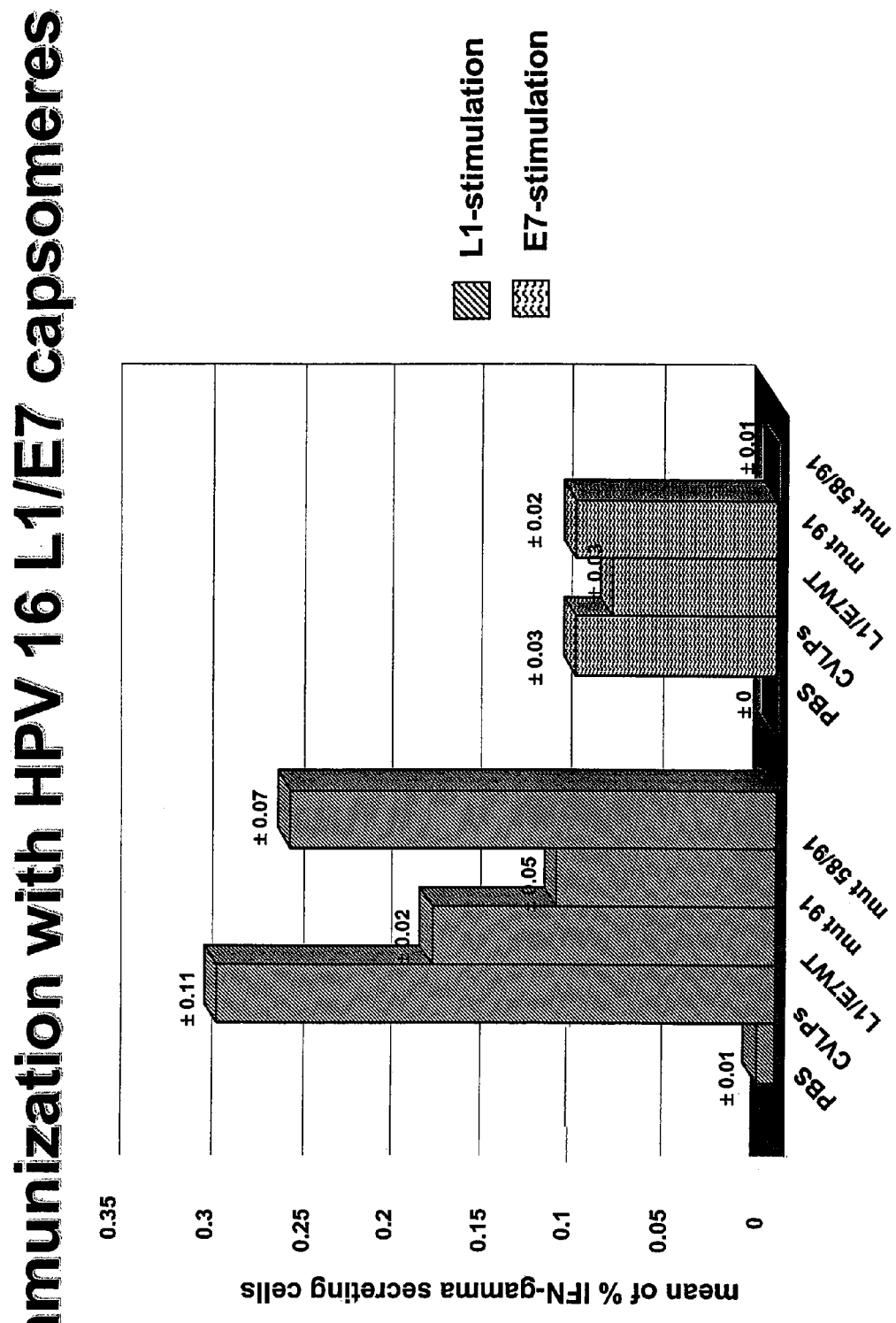
FIG. 6 demonstrates the generation of cytotoxic T-cell (CTL) response after immunization with L1-E7.
Figure 7:
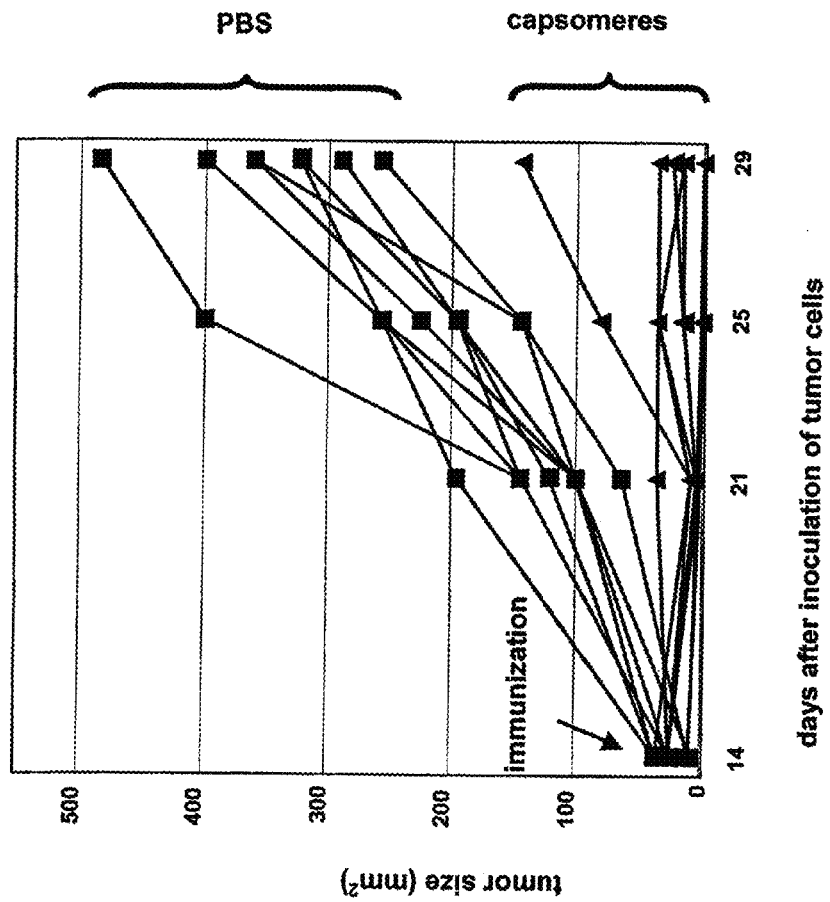
FIG. 7 graphically demonstrates that L1 capsomeres alone generate a CTL response that kills tumors expressing L1 antigen.

In order to facilitate an understanding of the invention, the following definitions are provided. Otherwise, all technical terms have their ordinary, art-recognized definitions.

Capsid protein: the structural protein of a virus, e.g., enveloped or non enveloped, which constitutes the capsid structure. Generally, there are several capsid proteins which are often described by whether they are the predominant (major) constituent or lesser (minor) constituent of capsid structure.

Major capsid protein or L1 protein: the structural protein of papillomavirus (PV) which constitutes the major portion of the PV capsid structure. This protein has reported application in the preparation of HPV (human papillomavirus) vaccines and as a diagnostic agent. Minor capsid protein or L2 protein: the structural protein of papillomavirus (PV) which constitutes the minor portion of the PV capsid structure. The nucleic acid sequence for this protein is shown in FIGS. 1 through 4 (SEQ ID NO. 1, SEQ ID NO. 2, SEQ ID NO. 3, and SEQ ID NO. 4, respectively).

Virus-like particles or VLPs: the capsid-like structures that result upon expression and assembly of a papillomavirus L1 DNA sequence alone or in combination with an L2 DNA sequence. VLPs are morphologically and antigenically similar to authentic virions. VLPs may be produced in vivo, in suitable host cells or may form spontaneously upon purification of recombinant L1 and/or L2 proteins. Additionally, they may be produced using capsid proteins L1 and L2, fragments or mutated forms thereof, e.g., L1 or L2 proteins that have been modified by the addition, substitution or deletion of one or more amino acids. L1 and L2 mutants that fall within the scope of the present invention are those that upon expression present at least one native PV conformational epitope. Methods to assemble VLPs are known in the art.

Correctly-folded L1 or L2 protein: L1 or L2 protein, fragment thereof, or mutated form thereof, (either monomeric, in the form of small oligomers (dimers-tetramers) or capsomeres), which, upon expression, assumes a conformational structure that presents one or more conformational HPV L1 or L2 epitopes present on native viral capsids or VLPs and is suitable for assembly into VLPs. In the present invention, a correctly folded HPV L1 or L2 protein will present one or more HPV L1 or L2 conformational epitopes.

Conformational L1 or L2 HPV epitope: an epitope expressed on the surface of correctly-folded L1 or L2 protein which is also expressed by an L1 or L2 protein or fragment, or mutated form thereof, which is also expressed by an L1 or L2 protein of a corresponding wild-type, infectious HPV. It is well accepted by those skilled in the art that the presentation of conformational epitopes is essential to the efficacy (both as prophylactic and diagnostic agents) of HPV L1 or L2 protein immunogens.

Conformational Neutralizing L1 or L2 HPV epitope: an epitope expressed on the surface of correctly-folded L1 protein, fragment or mutated form thereof, which is also expressed by an L1 or L2 protein of a corresponding wild-type, infectious HPV, and which elicits neutralizing antibodies. It is well accepted by those skilled in the art that the presentation of conformational neutralizing epitopes is essential to the efficacy (both as prophylactic and diagnostic agents) of HPV L1 or L2 protein immunogens.

Conformational antibody: an antibody that specifically binds an epitope expressed as a correctly-folded L1 or L2 protein but not on denatured L1 or L2 protein.

Capsomere: this refers to a structure that makes up the larger viral capsid structure that is generally a polymer of one or more types of capsid proteins. In the case of HPV, a native capsomere comprises a pentamer of L1 capsid proteins that may be associated with one L2 capsid protein.

Capsid: this refers to the structural portion of a virus, e.g., HPV, that is comprised of capsomeres. In the case of HPV, the viral capsid is comprised of 72 capsomeres.

A "chimeric protein" is created when two or more genes that normally code for two separate proteins recombine, either naturally or as the result of human intervention, to code for a protein that is a combination of all or part of each of those two proteins.

The present invention provides a chimeric protein comprising a papillomavirus L2 capsid polypeptide having a papillomavirus capsid protein L1-binding domain and a second polypeptide comprising at least one immunogenic epitope, wherein the polypeptides are fused at their amino or carboxy terminal ends. The papillomavirus L2 capsid polypeptide can include the full-length papillomavirus L2 capsid protein as well as truncated versions of the L2 protein containing an L1 capsid protein binding region. Alternatively, the present invention provides a chimeric protein comprising a papillomavirus L1 protein linked by at least one amino acid to a second polypeptide comprising at least one immunogenic epitope. The papillomavirus L1 capsid polypeptide can include the full-length papillomavirus L1 capsid protein as well as truncated versions of the L1 protein.

Preferred vaccine formulations of this type include capsomeres comprised of truncated L1 with or without L2 viral proteins. Particularly preferred capsomeres are comprised of truncated L1 proteins. Truncated proteins contemplated by the invention include those having one or more amino acid residues deleted from the carboxy terminus of the protein, or one or more amino acid residues deleted from the amino terminus of the protein, or one or more amino acid residues deleted from an internal region (i.e., not from either terminus) of the protein. Preferred capsomere vaccine formulations are comprised of proteins truncated at the carboxy terminus.

A papillomavirus L1 or L2 protein binding region indicates any sequence of amino acids or arrangement of amino acids in three dimensions (not necessarily a linear amino acid sequence) that has the ability to specifically but non-covalently associate with another sequence of amino acids or arrangement of amino acids in three dimensions. Specific binding may include binding that is mediated by ionic interactions, hydrophobic interactions, or any other method of interaction that is stronger than general, i.e. non-specific, protein-protein interactions. Specific binding can also be defined as a protein/protein association that survives treatments with such disruptive reagents such as, for example, moderate levels of salts, weak detergents, and moderate levels of urea.

In another embodiment, papillomavirus L2 capsid polypeptides of this invention may also include polypeptides that are substantially identical to a portion of L2 containing an L1 binding domain, such as but not limited to SEQ ID. Nos. 14 shown in FIGS. 1-4. By "substantially identical" it is meant a polypeptide having a sequence that is at least 85%, preferably 90%, and more preferably 95% or more identical to the sequence of the reference amino acid and containing a region capable of binding to an L1 protein. For polypeptides, the length of the reference polypeptide sequence will include an L1 binding region and will generally be from at least about 7 amino acids to about 455 amino acids. More preferred are lengths below 100 amino acids, and most preferred are lengths of about 44 amino acids. These binding domains are shown in FIG. 5 and Table 3, discussed in further detail below. Sequence identity can be measured using sequence analysis software (e.g., Sequence Analysis Software Package of the Genetics Computer Group, University of Wisconsin Biotechnology Center, 1710 University Avenue, Madison, Wis. 53705).

Included in the chimeric proteins of the present invention is a second polypeptide that comprises a polypeptide containing at least one immunogenic epitope. The polypeptide can include a full-length protein or any portion thereof that is at least about 5 amino acids in length and has a useful function, including, but not limited to, the ability to elicit an immune response, elicit an immunomodulatory effect (e.g. an immunomodulator that stimulates or reduces the immune response), effect enzyme activity, or otherwise effect cell division, differentiation, development and cell death. Preferred polypeptides are viral oncogenic proteins or fragments thereof containing an immunogenic epitope, including but not limited to T cell defined tumor antigens, many of which are described in the art, for example see Van den Eynde, B. J., et al., Current Opinion in Immunology, 9:684-693 (1997), which is incorporated herein by reference in its entirety. Preferred antigens include those that are encoded by genes that are activated in a number of tumors of various histological types. Prototype antigens of this type are those encoded by the gene P1A in the mouse and by the MAGE genes in humans. Of these genes, preferred are P1A, MAGE-1, MAGE-3, MAGE-6, BAGE, GAGE-1/2, GAGE-8 to 6, RAGE-1, GnTV, mucin. Other preferred tumor antigens include tumor antigens arising from mutations, and include tumor antigens arising from mutations in mouse genes, such as for example mutations in connexin-37, ribosomal protein L9, gag IAP, gp70 env MuLV, p53, various ras mutations, DEAD box helicase p68, c-akt, and mutations in human genes, such as for example mutations in MUM-1, CDK4, .beta.-catenin, HLA-A2, bct-abl (b3a2), CASP-8, and KIAA0205. Other potential epitopes include, but are not limited to, viral proteins, either in their entirety or as fragments, such as, but not limited to E6/E7 proteins of papillomavirus, herpes virus capsid and early proteins, and respiratory synctial virus neutralizing epitopes. In instances where L1 alone is used the second polypeptide is linked to L1 by one or more amino acids.

Preferably, immunogenic epitopes are those that confer protective immunity, allowing a mammal or other animal to resist (delayed onset of symptoms or reduced severity of symptoms), as the result of its exposure to the antigen of a pathogen, disease or death that otherwise follows contact with the pathogen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. "Humoral immunity" is the result of IgG antibodies and IgM antibodies in serum. "Cellular immunity" can be achieved through cytotoxic T lymphocytes or through delayed-type hypersensitivity that involves macrophages and T lymphocytes, as well as other mechanisms involving T cells without a requirement for antibodies. The primary result of protective immunity is the destruction of the pathogen or inhibition of its ability to replicate itself.

The present invention also includes a complex comprising the chimeric protein of the present invention further comprising a papillomavirus L1 polypeptide, protein or fragment thereof, or substantially identical protein or fragments. Papillomavirus L1 polypeptides of the present invention include polypeptides that retain their ability to bind to papillomavirus L2 polypeptides of the present invention. The complexes of the present invention include L1 capsid protein fragments that upon expression present conformational, neutralizing epitopes. These fragments can include full length papillomavirus L1 capsid proteins as well as internal, carboxy- and amino-terminal deletions, and proteins having specific cystein mutations that prevent assembly into VLPs. The deletion may range in size from 1 to about 100 amino acids, preferably 1 to 50 amino acids, and more preferably from about 1 to 25 amino acids. It is essential that the deletion still allow for the expression of a capsid protein, e.g., HPV L1 protein, that when expressed in fused or non-fused form presents at least one conformational, neutralizing epitope.

Complexes of the present invention will most preferably be in the form of a capsomere. Capsomeres of the present invention will generally have a stoichiometry of about one chimeric protein of the present invention to about five papillomavirus L1 capsid proteins, although capsomeres of greater or lesser stoichiometry are also contemplated.

In another embodiment, the capsomeres of the present invention can be assembled into a VLP. In this embodiment, assembly can be performed using methods known in the art. The present invention includes methods to assemble a VLP using capsomeres of the present invention at acidic to physiological pH. Most preferred are methods to assemble VLPs using capsomeres of the present invention at physiologic pH. In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

In some cases a linker of non-antigenic amino acids may be inserted between the first polypeptide and the second polypeptide, to further enhance the antigenicity of the chimeric protein or portions thereof or for any other beneficial effect on the chimeric protein. The process involves constructing a DNA plasmid for fusing second polypeptide genes to full length or fragments of the first polypeptide, using oligonucleotide probes and polymerase chain reaction (PCR) methodology.

The fusion between the first polypeptide and the second polypeptide to create a chimeric protein of the present invention can occur at either the amino- or carboxy-terminus of the second polypeptide. However, it is most preferable to link the second polypeptide comprising at least one immunogenic epitope at the second polypeptide's carboxy-terminus to the amino-terminus of the first polypeptide comprising a papillomavirus L2 polypeptide, yielding a chimera comprising the second polypeptide on the amino terminal end of the chimeric protein and the first polypeptide comprising the L2 polypeptide on the carboxy terminal end of the chimeric protein. The inventors believe, without being bound by theory, that such a fusion, where it involves amino-terminus truncated L2 proteins, has a greater ability to retain conformational folding of the L2 polypeptide.

In one aspect, the present invention relates to the expression of a viral capsid protein, and more preferably a papillomavirus L1 or L2 capsid protein or fragment, and most preferably a papillomavirus L2 capsid protein or fragment thereof as a glutathione-S-transferase (GST) fusion protein. The GST protein may be fused at the amino-terminal or carboxy-terminal portion of the viral capsid protein or fragment thereof.

In preferred embodiments, the GST protein is fused to the amino-terminus of an HPV L2 polypeptide of the present invention thus leaving the carboxy-terminus for appending the additional epitope. However, it is hypothesized that fusion to the carboxy-terminus will also yield capsid proteins capable of binding to papillomavirus L1 proteins of the present invention.

Fusion of GST to viral capsid proteins is advantageous in that the expression product can easily be purified by glutathione sepharose chromatography. Further, if it is desired to remove the GST moiety from the chimeric protein or capsomeres of the present invention, methods known in the art can be utilized to do so. For example, GST proteins may be incubated with thrombin, by methods known in the art, to cleave the GST moiety.

Viral proteins of the present invention may be derived from any papillomaviruses. More preferred are papillomaviruses and even more preferred are any human papillomavirus. Many HPV L1 and L2 DNAs have been reported in the literature and are publicly available. (See, e.g., Baker, Sequence Analysis of Papillomavirus, Genomes, pp. 321-384; Long, et al., U.S. Pat. No. 5,437,931; Cole, et al., J Mol. Biol., 193:599-608 (1987); Danos, et al., EMBO J, 1:231-236 (1982); Cole, et al., J Virol., 38(3):991-995 (1986)). Also, it is well known that HPV L1 and L2 DNAs exhibit significant homology to L1s and L2s of different serotypes of HPV. Therefore, a desired HPV L1 or L2 DNA can easily be obtained, e.g. by the use of a previously reported HPV L1 or L2 DNA or a fragment thereof as a hybridization probe or as a primer during polymerization chain reaction (PCR) amplification. Indeed, numerous HPV L1 and L2 DNAs have been cloned and expressed.

Most preferably, the HPV L1 or L2 DNA in the subject invention will be derived from an HPV which is involved in cancer or condylomata acuminata, e.g., HPV-16, HPV-18, HPV-31, HPV-33, HPV-35, HPV-39, HPV-45, HPV-51, HPV-52, and HPV-56 are involved in cancer, and HPV-6, HPV-11, HPV-30, HPV-42, HPV-43, HPV44, HPV-54, HPV-55, and HPV-70, are involved in warts. However, the subject capsid proteins may be produced using any desired HPV L1 DNA.

Virus particles can also be isolated for a particular papillomavirus type, the DNA cloned, and the nucleic acid sequences encoding L1 or L2 proteins isolated. Methods for isolation of viral particles and cloning of virus DNAs have been reported. (See, e.g., Heilman, et al., J Virology, 36:395-407 (1980); Heaudenon, et al., Nature, 321:246-249 (1986); Georges, et al., J Virology, 51:530-538 (1984); Kremsdorf, et al., J Virology, 52:1013-1018 (1984); Clad, et al., J Virology, 118:254-259 (1982); DeVilliers, et al., J Virology, 40:932-935 (1981); and European Patent Application 0,133,123.))

Alternatively, the L1 or L2 protein for a particular human papillomavirus can be isolated, the amino acid sequence determined and nucleic acid probes constructed based on the predicted DNA sequence. Such probes can be utilized in isolating the L1 gene from a library of the papillomavirus DNA. See, e.g., Suggs, et al., PNAS, 78(11):6613-6617 (1981) and Young and Davis, PNAS, 80:1194 (1983).

Proteins and capsomeres of the present invention can be produced in a variety of ways, including production and/or recovery of natural proteins, production and/or recovery of recombinant proteins, and/or chemical synthesis of the proteins. The proteins and polypeptides of the present invention will be expressed preferably in a prokaryotic microbial host, e.g., bacteria such as E. coli, that can be cultured under conditions that favor the production of capsid proteins. This will largely depend upon the selected host system and regulatory sequences contained in the vector, e.g., whether expression of the capsid protein requires induction. Proteins and polypeptides of the present invention may also be expressed in any host cell that provides for the expression of recoverable yields of the polypeptides in appropriate conformation. Suitable host systems for expression of recombinant proteins are well known and include, by way of example, bacteria, mammalian cells, yeast, and insect cells. A preferred expression system comprises the E. coli expression system used in the Examples, as this system provides for high capsomere yields. However, HPV L1 and L2 proteins, as well as other viral capsid proteins, can be produced in other systems.

Suitable vectors for cloning and expressing polypeptides of the present invention are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

Baculovirus systems offer the advantage that a large percentage of cells can be induced to express protein due to the use of infection rather than transfection techniques. While baculovirus is an insect virus and grows in insect cells (Sf9), these cells retain many of the eukaryotic mechanisms for processing of proteins including glycosylation and phosphorylation which may be important for generating proteins of appropriate conformation. Baculovirus vector systems are known in the art. (See, e.g., Summers and Smith, Texas Agricultural Experimental Bulletin, No. 1555 (1987); Smith, et al., Mol. Cell. Biol., 3:2156-2165 (1985); Posse, Virus Research, 5:4359 (1986); and Matsuura, J Gen. Virol., 68:1233-1250 (1987.)) Also, it has been reported that baculovirus-infected cells express HPV L1 proteins exhibiting the appropriate conformation. However, for the reasons already identified, bacterial expression and, more preferably, expression in E. coli, of a GST-L1 protein fusion is preferred.

For expression in an appropriate expression system, an L1 or L2 nucleic acid encoding a polypeptide of the present invention is operably linked into an expression vector and introduced into a host cell to enable the expression of the L1 protein by that cell. The gene with the appropriate regulatory regions will be provided in the proper orientation and reading frame to allow for expression. Methods for gene construction are known in the art. (For example, Molecular Cloning, A Laboratory Manual, Sambrook, et al., eds., Cold Spring Harbor Laboratory, Second Edition, Cold Spring Harbor, N.Y. (1989) describes general molecular biology techniques and is incorporated by reference in its entirety. Another source are the references cited herein.)

A wide variety of transcriptional and regulatory sequences may be employed. The signals may be derived from viral sources, where the regulatory signals are associated with a particular gene which has a high level of expression. That is, strong promoters, for example, strong bacterial, viral or mammalian promoters maybe utilized. In this manner, the optimum conditions for carrying out the invention include the cloning of the L1 gene into an expression vector that will overexpress conformationally-dependent virus-neutralizing epitopes of the L1 protein in transfected or infected target cells (E. coli).

The present invention also includes polynucleotides that encode chimeric proteins and complexes/capsomeres of the present invention. Accordingly, any nucleic acid sequence, which encodes the amino acid sequence of chimeric proteins and complexes/capsomeres of the present invention, can be used to generate recombinant molecules that express chimeric proteins and complexes/capsomeres of the present invention. It will be appreciated by those skilled in the art that as a result of the degeneracy of the genetic code, a multitude of nucleotide sequences encoding chimeric proteins and complexes/capsomeres of the present invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring chimeric proteins and complexes/capsomeres of the present invention, and all such variations are to be considered as being specifically disclosed.

Although nucleotide sequences which encode chimeric proteins and complexes/capsomeres of the present invention and its variants are preferably capable of hybridizing to the nucleotide sequence of the naturally occurring chimeric proteins and complexes/capsomeres of the present invention under appropriately selected conditions of stringency, it may be advantageous to produce nucleotide sequences encoding chimeric proteins and complexes/capsomeres of the present invention possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GRBP and its derivatives without altering the encoded amino acid sequences include the production of RNA transcripts having more desirable properties, such as a greater half-life, than transcripts produced from the naturally occurring sequence.

Chimeric proteins and capsomeres of the present invention have application in both prophylactic and therapeutic vaccines and diagnostics. The suitability of the chimeric proteins and capsomeres produced according to the invention for use as vaccines or as diagnostic agents can be confirmed by reaction with antibodies or monoclonal antibodies which react or recognize conformational epitopes present on the intact vision and based on their ability to elicit the production of neutralizing antiserum. Suitable assays for determining whether neutralizing antibodies are produced are known to those skilled in the art. This is an essential characteristic of HPV capsid proteins or other viral capsid proteins, which are to be used in HPV or other viral vaccines. In this manner, it can be verified whether the polypeptides of the present invention will elicit the production of anti-HPV neutralizing antibodies. Thus, other expression vectors and expression systems can be tested for use in the invention.

As discussed, the capsid proteins and stable forms thereof produced according to the present invention can be utilized to detect, diagnose, serotype, and treat papillomavirus infection. When used for diagnosis or serotyping, capsid proteins, e.g., polypeptides produced according to the invention may be labeled using any of a variety of labels and methods of labeling. Examples of types of labels, which can be used in the present invention, include, but are not limited to, enzyme labels, radioisotopic labels, non-radioactive isotopic labels, fluorescent labels, toxin labels, and chemiluminescent labels. Those of ordinary skill in the art will know of other suitable labels which may be employed in accordance with the present invention. The binding of these labels to viral capsid proteins, e.g., in the form of capsomeres, can be accomplished using standard techniques commonly known to those of ordinary skill in the art. Typical techniques are described by Kennedy, et al., Clin. Chim. Acta, 70:1-31 (1976), and Schurs, et al., Clin. Chim. Acta, 81:140 (1977). Coupling techniques mentioned in the latter are the glutaraldehyde method, the periodate method, the dimaleimide method, the m-maleimidobenzoyl-N-hydroxy-succinimide ester method, all these methods incorporated by reference herein.

The detection of the anti-HPV antibodies using the polypeptides of the present invention can be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other carriers suitable for binding proteins, or will be able to ascertain the same by use of routine experimentation.

The preferred aspect of the present invention, however, involves the development of viral vaccines, preferably HPV vaccines. The vaccines of the invention will contain chimeric proteins and/or capsomeres of the present invention in sufficient quantities to induce formation of neutralizing antibodies in the host contained in a pharmaceutically acceptable carrier.

It should be noted that use of adjuvants or carriers is not precluded by the present invention. Adjuvants are typically substances that generally enhance the immune response of a patient to a specific antigen. Suitable antigens include, but are not limited to, other bacterial cell wall components, aluminum based salts, calcium based salts, silica, polynucleotides, toxins, such as cholera toxin, toxoids, such as cholera toxoid, serum proteins, other viral coat proteins, other bacterial-derived preparations, block copolymer adjuvants, such as Hunter's TITERMAX adjuvant (Vaxcel™, Inc., Norcross, Ga.); Ribi adjuvants (available from Ribi ImmunoChem Research, Inc., Hamilton, Mont.) and saponins and their derivatives, such as Quil A (available from Superfos Biosector A/S, Denmark). Carriers are typically compounds that increase the half life of a composition in the treated patient. Suitable carriers include, but are not limited to, polymeric controlled release formulations, biodegradable implants, liposomes, bacteria, viruses, oils, esters and glycols.

The present invention includes polypeptides that elicit an immune response to an HPV antigen in a patient. An elicited immune response may be either prophylactic, preventing later infection by the specific viral type targeted, or may be therapeutic, reducing the severity of disease. An immune response includes a humoral, i.e., antibody, response to that antigen and/or a cell mediated response to that antigen. Methods to measure an immune response are known to those skilled in the art. If one or both types of immune response are present, they may protect a patient from the disease caused, for example, by the agent from which the composition was derived. In accordance with the present invention, the ability of an composition to protect from disease refers to the ability of a capsomere or chimeric protein of the present invention to treat, ameliorate and/or prevent disease caused by the disease causing agent or cross reactive agent, preferably by eliciting an immune response against an antigen derived from the disease causing agent and contained within a protein or capsomere of the present invention. It is to be noted that a patient may be protected by a composition of the present invention even without the detection of a humoral or cell-mediated response to the composition. Protection can be measured by methods known to those skilled in the art.

As more than one HPV type may be associated with HPV infections, the vaccines may comprise stable HPV capsid proteins derived from more than one type of HPV. For example, as HPV 16 and 18 are associated with cervical carcinomas, therefore a vaccine for cervical neoplasia may comprise VLPs of HPV 16; of HPV 18; or both HPV 16 and 18. In fact, a variety of neoplasia are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes (see, e.g., Kremsdorf, et al., J Virol., 52:1013-1018 (1984); Beaudenon, et al., Nature, 321:246-249 (1986); Heilman, et al., J Virol., 36:395-407

(1980); and DeVilliers, et al., J Virol., 40:932-935 (1981)). Thus, the subject vaccine formulations may comprise a mixture of capsid proteins or fragments derived from different BPV types depending upon the desired protection.

Yet another aspect of the present invention is a method to elicit an immune response to a chimeric protein or capsomere of the present invention in a patient, comprising administering to the patient a composition of the present invention. The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.001 mg to about 1 mg protein. Single or multiple dosages can be administered.

Administration of the subject capsid protein-containing vaccines may be effected by any pharmaceutically acceptable means, e.g., parenterally, locally or systemically, including by way of example, oral, intranasal, intravenous, intramuscular, and topical administration. The manner of administration is affected by factors including the natural route of infection. The dosage administered will depend upon factors including the age, health, weight, kind of concurrent treatment, if any, and nature and type of the particular viral, e.g., human, papillomavirus. The vaccine may be employed in dosage form such as capsules, liquid solutions, suspensions, or elixirs, for oral administration, or sterile liquid formulations such as solutions or suspensions for parenteral or intranasal use.

EXAMPLES

The invention is further illustrated by the following non-limited examples. All scientific and technical terms have the meanings as understood by one with ordinary skill in the art. The specific examples which follow illustrate the methods in which the chimeric compositions of the present invention may be prepared and used and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

Example 1

HPV 11 Bacterially Expressed L1 Protein Reacts with Conformational Antibodies

See, Li, M., et al., J. Virol., 71:2988-2995 (1997), which is hereby incorporated by reference.

Example 2

Co-Expression and Purification of HPV11 L1 and L2 Proteins from *E. Coli*

HPV11 L1 and HPV11 glutathione-S-transferase (GST) L2 fusion proteins were co-expressed in *E. coli* by the following methods. It is noted that the particulars of this cloning and purification process are not essential to the invention and many different methods to generate the same results will be apparent to those skilled in the art. HPV11 L1 protein was expressed from a pET17b vector that confers ampicillin resistance (available from Novagen, Madison Wis.). HPV11L2 (or portions thereof) was expressed as a GST fusion protein from the vector pXA/BN, which confers chloramphenicol resistance, and also facilitates purification of L2 by glutathione-sepharose chromatography. L2 and L1 expressing vectors are co-transformed into competent *E. coli* BL21(DE3) (available from Novagen, Madison Wis.) under chloramphenicol and ampicillin selection. A single isolated colony of co-transformed bacteria was inoculated into 5 milliliter (mL) 2×YT media supplemented with ampillicin (100 .mu.g/mL) and chloramphenicol (40 .mu.g/mL) and grown overnight at 37.degree. C. Fresh medium (5 mL) was inoculated with 0.1 mL of this overnight culture and allowed to grow 5 to 6 hours at 37.degree. C. This culture was used to inoculate larger scale cultures (one 5 mL starter culture per liter) which were subsequently grown at 37.degree. C. to an OD600 of approximately 0.2. Cultures were then induced with 0.2 millimolar (mM) IPTG (available from Fisher Scientific, Denver) for 5 to 6 hours or cooled to 25.degree. C., induced with 0.2 mM IPTG and grown overnight at 25.degree. C. Cultures were centrifuged to yield cell pellets, which were resuspended in lysis buffer (40 mM Tris-Cl pH 8.0, 0.2 M NaCl, 5% glycerol, 1 mM EDTA, 5 mM DTT) supplemented with protease inhibitors (5 .mu.g/mL pepstatin, 2 .mu.g/ml leupeptin and 2 mM phenylmethylsulfonyl fluoride). The following steps were carried out at 4.degree. C. Cells were lysed by the addition of 0.5 mg/ml lysozyme and incubated for 20 minutes followed by the addition of 0.1% deoxycholate and incubating for an additional 10 minutes. The lysates were then treated with 10 units/ml DNAse I in the presence of 5 mM MgCl2 for 30 minutes. All previously mentioned reagents are available from Fisher Scientific. Lysates were briefly sonicated, then centrifuged at 17,000 G for one hour and the supernatant was passed over a 10 mL bed volume glutathione sepharose column. (available from Pharmacia). The columns were washed with buffer L (40 mM Tris-Cl, pH 8.0, 0.2 M NaCl, 1 mM EDTA, 2 mM DTT) until no protein was detectable in the wash (approximately 20 bed volumes). To purify L1+GST-L2 complexes, bound proteins were eluted with 10 mM reduced glutathione in buffer L. The eluates were concentrated using Centriplus concentrators (Amicon). To further purify L1+L2 complexes from contaminating bacterial proteins, free L2 and L2 degradation products, eluted proteins were subjected to size exclusion fast pressure chromatography (FPLC) using a HiLoad Superdex 200 gel filtration column (Pharmacia). FPLC fractions containing complexes were pooled and further concentrated as outlined above. Protein complexes were analyzed by SDS-PAGE followed by Coomassie blue staining or immunoblotting. For densitometric analysis on Coomassie-stained gels, images were captured using a fluor-S MultiImager (Bio-Rad) with Quantity One software (Bio-Rad) and quantitated using ImageQuant software (Molecular Dynamics). Using this strategy, L1 will be present upon elution from glutathione-sepharose only if it is bound to GST-L2. If desired, GST can be cleaved from the complex by digesting the glutathione sepharose with thrombin (available from Sigma, St. Louis).

Using these procedures, up to 5 mg of partially purified L1+L2 complexes were obtained per liter of bacterial culture.

Example 3

Cloning and Construction of Deletion and Site-Directed Mutants of HPV 11 L2 Capsid Protein; Identification of an HPV11 L1 Binding Domain Within HPV11 L2

Full length HPV11 L1 DNA. Full length HPV11 DNA sequence was obtained by PCR amplification from plasmid pVL11L1 (obtained by methods outlined in Rose, et al., J. Virol, 67:1936-44 (1993)) with the forward primer 5'-GCCGCGAAGCTTCATATGTGGCGGCCTAGCGCAG (SEQ ID NO. 5), containing an NdeI restriction enzyme site at the initiator methionine codon, and the reverse primer, 5'-GGGCCTGGATCCAGATCTCACAACACACACTGACACAC (SEQ ID NO. 6). The PCR-amplified fragment was subcloned into a PCR II vector (Invitrogen), using manufacturer's protocols. An NdeI/BstX1 fragment encompassing the amplified sequences was excised from this intermediate vector, purified and then ligated to similarly-digested pET17B vector (Novagen) to generate pET17b-HPV11 L1.

b. HPV L2 DNA. The pXA/BN-based vectors, used for expressing HPV11 GST-L2 fusion proteins and all other GST-L2 fusion protein derivatives described within this example, were engineered from the original pAC vector described by Chen, et al., Embo J., 17:3233-40 (1998), to incorporate the multiple cloning site of pGEX-4T-2 (Pharmacia). Originally, full-length HPV11 L2 DNA was obtained by PCR amplification from a PCR II vector (Invitrogen) containing full-length HPV11 L2 DNA (PCR11/L2) with a forward primer 5'-GGGGGATCCATGAAACCTAGGGCACGC (SEQ ID NO. 7), containing a BamHI restriction site at the 5' terminus and a reverse primer, 5'-GGGGCGGCCGCCTAG-GCCGCCACATCTG (SEQ ID NO. 8), containing a NotI restriction site at the 3' terminus. The PCR-amplified fragment was subcloned into a PCR II vector and then a BamH1/NotI fragment excised from this intermediate vector was ligated to a similarly digested pGEX-4T-2. The pGEX-4T-2 vector containing L2 was used as a source of BamHI/NotI fragment to subclone into pXA/BN to generate pXA/BN-HPV11 L2. A similar strategy was used to construct the initial deletion mutants of HPV11 L2 encompassing amino acids 1-156, 1-309, 157-309, 157-455, and 313-455. The primer pairs used for PCR amplification of these subsequent deletion mutants are given in Table 1. For subsequent deletion mutants, the HPV11 L2 DNA was amplified from pXA/BN-HPV11 L2 and subcloned into pCR2.1-TOPO vector (Invitrogen), according to the manufacturer's instructions. BamHI/NotI fragments encompassing the amplified sequences were excised from these intermediate vectors and subcloned into pXA/BN. This strategy was also used to clone sequences corresponding to the carboxy-termini of various papillomavirus L2s with the exception of BPV1 L2, which was cloned as a BamHI/XhoI fragment. These full-length L2 sequences were aligned with the full-length sequence of HPV11 L2 using Vector NTO AlignX software (InforMax) to define candidate amino acids for incorporation into each construct (Table 1). Overlap extension PCR with paired mutagenic primers was used for the site directed mutagenesis of specific HPV11 L2 amino acids. The sequence of these mutagenic primers (made by methods described in Horton, et al., Biotechniques, 8:528-35 (1990) and Yon, J. and M. Fried, Nucleic Acids Res, 17:4895 (1989)) and is given in Table 1; the forward and reverse outside primers used to amplify a fragment containing the mutated sequence were 5'-GGGCTGGCAAGCCACGTTTGGTC (SEQ ID NO. 9) and 5'-AATTCCAGATCTATACACTCCGCTATCGC (SEQ ID NO. 10), respectively. Cloning of the amplified sequences into pXA/BN was performed as outlined above. The sequence of all DNA subjected to PCR amplification was verified by sequencing.

TABLE 1

Primers used for constructing deletion and site-directed mutants of HPV11 L2.

| Plasmid | Forward primer[a] | Reverse primer |
|---|---|---|
| pXA/BN-HPV11L2/1-156 | GGGGGATCCATGAAACCTAGGGCACGC (SEQ ID NO. 11) | GGGCGGCCGCATTTTGAAACACACTAGTGG (SEQ ID NO. 12) |
| pXA/BN-HPV11L2/1-309 | GGGGGATCCATGAAACCTAGGGCACGC (SEQ ID NO. 13) | GGGGCGGCGGCTCCACTGCGTGTGTACATG (SEQ ID NO. 14) |
| pXA/BN-HPV11L2/157-309 | GGGGGATCCCCCCTGTTTACAGAACCG (SEQ ID NO. 15) | GGGGCGGCGGCTCCACTGCGTGTGTACATG (SEQ ID NO. 16) |
| pXA/BN-HPV11L2/157-455 | GGGGGATCCCCCCTGTTTACAGAACCG (SEQ ID NO. 17) | GGGGCGGCCGCCTAGGCCGCCACATCTG (SEQ ID NO. 18) |
| pXA/BN-HPV11L2/313-455 | CAAGGATCCGGTGCCCGCATACATTAT (SEQ ID NO. 19) | GGGGCGGCCGCCTAGGCCGCCACATCTG (SEQ ID NO. 20) |
| pXA/BN-HPV11L2/313-400 | CAAGGATCCGGTGCCCGCATACATTAT (SEQ ID NO. 21) | AATTCCGCGGCCGCTATGTCAGGCCCAGA (SEQ ID NO. 22) |
| pXA/BN-HPV11L2/346-455 | AATTCCGGATCCGATATTTATGCTGAA (SEQ ID NO. 23) | GGGGCGGCCGCCTAGGCCGCCACATCTG (SEQ ID NO. 24) |
| pXA/BN-HPV11L2/396-455 | AATTCCGGATCCTCTGGGCCTGACATA (SEQ ID NO. 25) | GGGGCGGCCGCCTAGGCCGCCACATCTG (SEQ ID NO. 26) |
| pXA/BN-HPV11L2/346-439 | AATTCCGGATCCGATATTTATGCTGAA (SEQ ID NO. 27) | AATTCCGCGGCCGCTGCAAAGTACCATGAGG (SEQ ID NO. 28) |
| pXA/BN-HPV11L2/396-439 | AATTCCGGATCCTCTGGGCCTGACATA (SEQ ID NO. 29) | AATTCCGCGGCCGCTGCAAAGTACCATGAGG (SEQ ID NO. 30) |

TABLE 1-continued

Primers used for constructing deletion and site-directed mutants of HPV11 L2.

| Plasmid | Forward primer[a] | Reverse primer |
|---|---|---|
| pXA/BN-HPV11L2/313-455/ AL417418EE | CTGTAACTCCTGAAGAACCTACAGGCCC (SEQ ID NO. 31) | GGGCCTGTAGGTTCTTCAGGAGTTACAG (SEQ ID NO. 32) |
| pXA/BN-HPV11L2/313-455/ A417E | CTGTAACTCCTGAATTACCTACAGGCCC (SEQ ID NO. 33) | GGGCCTGTAGGTAATTCAGGAGTTACAG (SEQ ID NO. 34) |
| pXA/BN-HPV11L2/313-455/ L418EE | CTGTAACTCCTGCTGAACCTACAGGCCC (SEQ ID NO. 35) | GGGCCTGTAGGTTCAGCAGGAGTTACAG (SEQ ID NO. 36) |
| pXA/BN-HPV11L2/313-455/ P413A | ACACCCTTTAGTGCTGTAACTCCTG (SEQ ID NO. 37) | CAGGAGTTACAGCACTAAAGGGTGT (SEQ ID NO. 38) |
| pXA/BN-HPV11L2/313-455/ P416A | GTCCTGTAACTGCTGCTTTACCTAC (SEQ ID NO. 39) | GTAGGTAAAGCAGCAGTTACAGGAC (SEQ ID NO. 40) |
| pXA/BN-HPV11L2/313-455/ P419A | ACTCCTGCTTTAGCTACAGGCCCTG (SEQ ID NO. 41) | CAGGGCCTGTAGCTAAAGCAGGAGT (SEQ ID NO. 42) |

[a]Primer sequences are given 5' to 3'; restriction sites within the primer are underlined; mutations within the primer are indicated in bold type.

TABLE 2

Other Papillomavirus L2 Expression Constructs used in this Application

| Virus | L2 amino acids incorporated | NCBI reference[a] | Forward primer[b] | Reverse primer |
|---|---|---|---|---|
| HPV6b | 316-459 | NC_001355 | AATTCCGGATCCGGGGCCCGCATTCATTATTTTTA (SEQ ID NO. 43) | AATTCCGCGGCCGCCTAGGCCGCCACATCTG (SEQ ID NO. 44) |
| HPV16 | 321-473 | NC_001526 | AATTCCGGATCCGGTGCTAAGGTACATTATTATTA (SEQ ID NO. 45) | AATTCCGCGGCCGCCTAGGCAGCCAAAGAGAC (SEQ ID NO. 46) |
| HPV33 | 319-467 | NC_001526 | AATTCCGGATCCGGAGCTAGAATACATTATTATC (SEQ ID NO. 47) | AATTCCGCGGCCGCCTAGGCCGCCACACGGAC (SEQ ID NO. 48) |
| HPV1a | 347-507 | NC_001356 | AATTCCGGATCCGGGCCACAAAGCCATTTTTAC (SEQ ID NO. 49) | AATTCCGCGGCCGCTTAAAAAAAAAATGTTTGCG (SEQ ID NO. 50) |
| HPV5 | 376-518[c] | NC_001531 | AATCCGGATCCGGGTCGCAAGTCCATTTTTAC (SEQ ID NO. 51) | AATTCCGCGGCCGCTCACAAATATTTTCTTC (SEQ ID NO. 52) |
| HPV12 | 360-518 | NC_001577 | AATTCCGGATCCGGATCACAGGTTCATTTTTATAG (SEQ ID NO. 53) | AATTCCGCGGCCGCTCACAAATATTTTCTTC (SEQ ID NO. 54) |
| COPV1 | 360-513 | NC_001619 | AATTCCGGATCCGGGCCACAAAGCCATTTTTAC (SEQ ID NO. 55) | AATTCCGCGGCCGCTTAAAAAAAAAATGTTTGCG (SEQ ID NO. 56) |

TABLE 2-continued

Other Papillomavirus L2 Expression Constructs used in this Application

| Virus | L2 amino acids incorporated | NCBI reference[a] | Forward primer[b] | Reverse primer |
|---|---|---|---|---|
| BPV1 | 316-469 | NC_01522 | AATTCCGGATCCGGA CCACAGCTACATGTCA GG (SEQ ID NO. 57) | CTCGAGTTAGGCAT GTTTCCGTTTTTTC GTTTC (SEQ ID NO. 58) |

[a]Sequences are the same as those given in the NCBI reference with the exception of the HPV5 isolate. The relevant amino acid changes within the putative L1-binding domain of HPV5 are indicated on FIG. 5.
[b]Primer sequences are given 5' to 3'; restriction sites within the primer are underlined . . . sup.
[c]Although primers were designed such that HPV5 amino acids 360 through 518 would be incorporated, only amino acids 376 through 518 are present due to the presence of a cryptic BamHI site at 5472 in the HPV5 isolate used for PCR amplification.

Example 4

Description of the L1 Binding Domain on HPV11 L2

The deletion mutants of HPV11 L2 described in Example 3 were co-expressed with HPV 11 L1 as described in Example 2. Similar levels of L1 were detected in whole cell lysates prepared from each co-expression prior to purification of L1+L2 complexes by SDS-PAGE followed by Coomassie Blue staining. The ability of each L2 protein to bind HPV11 L1 was determined by the presence or absence of L1 in the eluate from the glutathione sepharose column as measured by SDS-PAGE. The results of the co-expression assays indicate that an HPV11 L1 binding domain is contained within amino acids 396 through 439 near the C-terminus of L2. This L1 binding domain is distinct from the nuclear localization signal of HPV11 L2 comprised by amino acids 440 through 445.

TABLE 3

| L2 amino acids | Complex with L1 |
|---|---|
| 1-455 | Yes |
| 1-158 | No |
| 1-309 | No |
| 157-309 | No |
| 157-455 | Yes |
| 313-455 | Yes |
| 313-400 | No |
| 348-455 | Yes |
| 396-455 | Yes |
| 348-439 | Yes |
| 396-439 | Yes |

GST-HPV11 L2 fusion proteins used to define the HPV11 L1-binding domain of HPV11 L2. L2 amino acids incorporated into each fusion protein to form a complex with L1 in bacteria are indicated. The results from this experiment show that the HPV11 L1 binding domain is contained within amino acids 396 through 439 near the carboxy-terminus of L2.

Example 5

Identification of Critical Residues for L1/L2 Binding

In order to help identify specific residues within the 44 amino acid domain of L2 affecting L1 binding, as described in Example 4, the ability of HPV11 L1 to bind L2 proteins from eight different papillomavirus serotypes/species was determined. The carboxy terminal third of each L2 was utilized in coexpression assays as described in Example 2. Table 4 summarizes the results of this experiment. HPV11 L1 formed heterologous complexes with L2 proteins from other genital isolates (HPVs 6b, 16, and 33), from skin isolates (HPVs 5 and 12) and from a non-human isolate, COPV1. HPV11 L1 was unable to form a complex with either HPV1a or BPV1 L2 despite robust production of the L2 fusion protein in both cases. The stoichiometry between L1 and full-length GST-L2 fusion protein of the partially purified extracts of the heterologous complexes formed with the genital isolates was greater than 1:1 as was the case for the homologous complex. This stoichiometry was not found in partially purified extracts of heterologous complexes formed with the skin isolates or with COPV1. Instead, the L1:L2 stoichiometry is that the binding was weaker in the case of complexes formed between HPV11 L1 and L2 proteins from HPV 5 and 12 and COPV1, thus more unassociated L2 was detectable. Accordingly, binding of L1 by genital isolates was classified as strong, by the skin isolates and COPV1 as weak, and of HPV1a and BPV1 as undetectable.

TABLE 4

HPV11L1 interactions with L2 proteins from other papillomavirus

| Virus | Host | Location of infection (risk)[a] | Supergroup[b] | L1:L2[c] | Interaction with HPV11 L1[d] |
|---|---|---|---|---|---|
| HPV11 | Human | Genital tract (low) | A10 | >1:1 | Strong |
| HPV86 | Human | Genital tract low) | A10 | >1:1 | Strong |
| HPV16 | Human | Genital tract (high) | A9 | >1:1 | Strong |
| HPV33 | Human | Genital tract (moderate) | A9 | >1:1 | Strong |
| HPV10 | Human | Skin | E1 | ND | Undetectable |
| HPV5 | Human | Skin | B1 | <1:1 | Weak |
| HPV12 | Human | Skin | B1 | <1:1 | Weak |
| COPV1 | Dog | Oral | E | <1:1 | Weak |
| BPV1 | Cow | Skin | C1 | ND | Undetectable |

[a]Risk of genital tract isolates for progression to cervical carcinoma.
[b]Supergroup designation is that defined in Human Papillomaviruses 1997 (1) based on a phylogenetic tree computed from a consensus primer region of L1.
[c]Relative amounts of L1 to full-length GST = L2 fusion protein were determined by densitometric analysis of Coomassie blue-stained SDS PA gels.
[d]Strength of interaction with L1 is based on the ability to detect L1 by immunoblot analysis as well as the relative amounts of L1 and L2.
ND = not determined.

Example 6

Importance of Hydrophobic Residues 414-418

Inspection of the alignment in FIG. 5 does not reveal an obvious primary amino acid sequence unique to those L2 proteins that are capable of binding HPV11 L1. Instead, it was noted that the sequence segment bounded by conserved proline residues at 413 and 419 of HPV11 L2 is predominately hydrophobic without negatively charged residues in those L2 proteins classified as strong HPV11 L1 binders. In the case of weak binders, at least one negatively charged amino acid is present and in the case of both HPV1a and BPV1, where binding was undetectable, two negatively charged amino acids are present. Based on these observations, the inventors, without being bound by theory, speculate that disruption of this hydrophobic tract would disrupt HPV11 L1 binding. To test this hypothesis, alanine 417 and leucine 418 of HPV1 .mu.L2 were both changed to glutamines (AL417-418EE) and the ability of this mutant L2 protein to bind L1 was examined in co-expression assays, as described in Example 2. The double mutant L2 protein AL417-418EE was weakened in its ability to bind L1 with an L1:L2 of 1:3 as compared to 2:1 for the wild-type L2 protein. The A417E mutant displayed a slight disruption of L1 binding (L1:L2 was 1:1) while the L418E mutant L2 protein displayed no disruption in HPV11 L1 binding. These results support the importance of the hydrophobic tract between pralines 413 and 419 in HPV11 L1/L2 binding. Specifically, the introduction of two negatively charged residues at position 417 and 418 decreased L1/L2 binding.

Example 7

Importance of Conserved Proline Residues 413, 416 and 419 on L1/L2 Binding

Another feature of the sequence between residues 413 and 419 is the presence of three proline residues. All other L2 proteins examined in studies also contain three prolines in this region with the exception of BPV1 L2, which contains two prolines. To test the importance of prolines 413, 416, and 419 of HPV11 L2 in L1 binding each of these prolines was changed individually to alanine (P413A, P416A, and P419A) and the ability of these mutant L2 proteins to bind L1 was examined in coexpression assays as described in Example 2 and 8. Surprisingly, in all three cases substituting an alanine for a proline did not change the ratio of L1:L2 indicating that these mutations did not disrupt L1 binding.

Example 8

Biochemical Characterization of L1/L2 Binding as Hydrophobic

Inspection of the carboxy-terminal L1 binding domain of HPV11 L2 from FIG. 1 revealed a high percentage of hydrophobic residues (>50%). The results from Examples 3, 4, 5, 6 and 7 suggested that hydrophobic interactions are important in L1+L2 complex formation. To test the importance of hydrophobic interactions, the ability of salt, weak detergents and urea to disrupt the complex was analyzed. A complex of HPV11 L1 bound to HPV GST=L2(313455) was immobilized on glutathione sepharose beads and incubated with a series of buffers. The amount of L1 in each sample was determined by densitometric scanning of Coomassie-stained gels relative to samples treated with buffer L (described in Example 2) alone, representing the background level of L1 liberated from the complex (baseline) and samples treated with SDS-PAGE loading buffer, representing all bound proteins (100%). The relative amount of L1 released by each buffer treatment is averaged from three independent experiments. A complex of HPV11 L1 bound to HPV11 GST-L2 (313-455) was immobilized on glutathione sepharose beads. Equal fractions of these beads were subjected to the following buffer treatments: 1 or 2 M NaCl, weak detergents (1% NP-40, 1% NP-40+0.1% DOC), and urea (1 M, 1.5 M, 2 M, 2.5 M) for one hour at room temperature. Treated beads were then pelleted by centrifugation and samples of the supernatants were analyzed by SDS-PAGE and immunoblot for the presence of L1. Densitometric analysis on Coomassie stained gels was performed as previously described. It was found that the above treatments did not release significant amounts (<20%) of L1 from the complex. Even treatment with 5 M urea failed to completely disrupt the L1+L2 complex. Taken together, these results indicate that the L1/L2 binding is strong and likely mediated by hydrophobic interactions.

Example 9

In Vitro Assembly into VLPs of L1+L2 Capsomeres at Physiologic pH

The ability to purify L1 pentamers bound to L2 permitted study of the specific effects of the L2 capsid protein on the in vitro assembly of VLPs (virus-like particles, or capsids, from capsomeres of L1+L2). The in vitro assembly properties of HPV11 L1 alone in comparison to HPV11 L1+L2 complex was compared. A L1+GST=L2(313-455) complex was treated with thrombin to remove the GST moiety and the resulting L1+L2(313455) complex was dialyzed into assembly buffer at pH 5.2 or 6.8 alongside purified L1. The recipe for assembly buffer is as follows: 40 mM HEPES, pH 6.8, 0.5 M NaCl or 40 mM Na citrate, pH 5.2, 0.5 M NaCl. Samples were treated at room temperature for one hour, then samples were absorbed onto glow-discharged formvar/carbon-coated 400 mesh copper grids and stained with 2% uranyl acetate. Specimens were analyzed by transmission electron microscopy using a CM10 electron microscope (Phillips Electronic Instruments, Inc.) operating at 80 kV. Previously, acidic pH was demonstrated to yield the most consistent in vitro assembly results in the case of both HPV11 L1 and HPV16 L1. At pH 5.2, both L1 and L1+L2(313-455) assembled into T=1 VLPs. At pH 6.8, L1 alone was unable to assemble into VLPs and free pentamers or aggregated clumps of pentamers were predominately observed. By contrast, L1+L2(313-455) assembled into T=1 VLPs at pH 6.8. These results indicate that L2 facilitates capsid assembly at a more physiological pH.

Example 10

Stoichiometry of the HPV11 L1/L2 Associated Complex

Densitometric analysis of partially purified bacterial eluates yielded a L1:L2 ratio of approximately 2:1. However, initial eluates contain degradation and/or premature termination produces that originate from the L2 fusion protein as determined by anti-GST immunoblot analysis, as well as contaminating bacterial chaperone proteins GroEL and DnaK. To remove unbound GST-L2 and chaperones, glutathione sepharose eluates of HPV11 L1 bound to HPV11 GST-L2(313-455) were subjected to size exclusion chromatography as described in Example 2. The L1:L2 ratio in the resulting purified complexes was approximately 5:1. Thus, a single molecule of L2 associates with a pentamer of L1, a ratio analogous to that observed in polyomavirus VP1/VP2 interactions.

Example 11

Prophetic Example of Substituting an Oncogenic Protein into the Non-L1 Binding Domain of L2

In order to develop a therapeutic vaccine for treating established cervical carcinoma, the L1 binding protein can be fused to the desired immunotherapeutic protein, notably E7, thereby allowing its incorporation into a VLP. This approach offers certain advantages over strategies that utilize full-length L2 to incorporate the desired foreign sequence in vivo. As only a portion of L2 need be used (as small as 44 amino acids), longer foreign sequences can be introduced. Also, as every pentamer would have foreign sequence attached, it may be possible to incorporate 72 copies of the foreign sequence into a VLP. These features, coupled with the cost-effectiveness of a bacterial system, make this an appealing technology for chimeric VLP production.

Example 12

Preparation of HPV 16 L1/E7 Capsomeres

Chimeric capsomeric constructs comprised of L1 alone would preferably include additional non-L1 sequences at the carboxy terminus of L1. GST would be positioned at the amino terminus. The completed construct would then be GST-L1-X from amino to carboxy terminus. In the case of GST-L1-E7, spacer amino acids (greater than 1) are added at the carboxy terminus of L1 (which may be deleted for up to 29 amino acids) and 60-70 residues of E7 are fused in frame with L1. The completed construct is then recombinantly expressed in bacteria. GST-pentamers of L1 are then purified as described with the fused E7 appended. These pentamers, with or without GST, can then be used for immunization.

Example 13

Immunization with Capsomeres Induces L1-Specific CTLs and Antibodies

To test for L1-specific activity in vivo, a tumor rejection experiment was performed using C3 cells, which were established by transformation with the complete HPV16 genome. A total of 5.times.10.sup.5 cells per animal were inoculated into mice (n=10) (FIG. 7). When the tumors had reached a mean size of 15.+-0.3 mm.sup.2 at day 14, 10 mice were injected with 10 .mu.g of HPV16 L1 capsomeres and 10 mice with PBS. Tumor size (measured with a ruler) was determined 1 week after immunization and mice (with strong tumor growth) and of mice showing partial or total regression were removed, and splenocytes were cultured. CTL activity was analyzed by ELISPOT. Tumor size of the mice within a group were calculated as arithmetic means with standard error of the means (SEMs).

The foregoing description is considered as illustrative only of the principles of the invention. The words “comprise,” “comprising,” “include,” “including,” and “includes” when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

What is claimed is:

1. A complex comprising:
 a) a first polypeptide comprising a papillomavirus L2 capsid polypeptide or peptide fragment thereof;
 b) the first polypeptide further comprising papillomavirus capsid protein L1-interaction sequence(s) comprising a first motif of Pro-Xaa$_{(4)}$ to Xaa$_{(10)}$-Pro followed by a second motif of Phe-Xaa-Leu-His-Pro or Tyr-Xaa-Leu-His-Pro; and
 c) a second polypeptide comprising five papillomavirus L1 capsid polypeptide or five truncated papillomavirus capsid L1 that form a capsomere non-covalently bound to the first polypeptide the two polypeptides form a complex.

2. The complex of claim 1, wherein the papillomavirus capsid protein L1-interacting sequence is a papillomavirus capsid protein L2 motif selected from the group consisting of HPV6, HPV6a, HPV6b, HPV11, HPV16, HPV18, HPV30, HPV31, HPV33, HPV35, HPV39, HPV42, HPV43, HPV44, HPV45, HPV51, HPV52, HPV54, HPV55, HPV56, and HPV70 capsid protein L2 polypeptides.

3. The complex of claim 2, wherein the papillomavirus capsid protein L2 motif is selected from the group consisting of HPV6b, HPV11, HPV16, and HPV33 papillomavirus capsid protein L2 polypeptides.

4. The complex of claim 2, wherein the papillomavirus capsid protein L2 motif is an HPV11 papillomavirus capsid protein L2 polypeptide.

5. The complex of claim 1, wherein the papillomavirus capsid protein L1-interacting sequence comprises an amino acid sequence comprising SEQ ID NO:1 comprising [HPV11] identified at amino acid sequence positions 1-455, amino acid sequence positions 157-455, amino acid sequence positions 313-455, amino acid sequence positions 346-455, amino acid sequence positions 346-439, amino acid sequence positions 396-455 and amino acid sequence positions 413-419; SEQ ID NO:50 comprising [HPV5] identified at amino acid sequence positions 376-518 and amino acid sequence positions 466-508; amino acid sequences comprising SEQ ID NO:2, [HPV 6B] identified at amino acid sequence positions 413-419, and amino acid sequence positions 400-443; SEQ ID NO:54 comprising [HPV12] identified at amino acid sequence positions 360-518 and amino acid sequence positions 466-508; amino acid sequence comprising SEQ ID NO:3, [HPV 16] identified at amino acid sequence positions 417-423, and amino acid sequence positions 412-455; amino acid sequence comprising SEQ ID NO:4, [HPV 33] identified at amino acid sequence positions 423-429, and amino acid sequence positions 406-449; and substantially identical homologs thereof.

6. The complex of claim 1, wherein the complex is expressed in a bacterial expression system.

7. The complex of claim 1, further comprising a peptide having at least one immunogenic epitope.

8. The complex of claim 7, wherein one or more of the first polypeptide or the second polypeptide is fused at its amino- or carboxy-terminus to the peptide having at least one immunogenic epitope to form a chimeric polypeptide with one or more of the first polypeptide or the second polypeptide.

9. The complex of claim 8, wherein the chimeric polypeptide further comprises glutathione-S-transferase protein, and wherein the chimeric polypeptide is fused at its amino- or carboxy-terminus to the glutathione-S-transferase protein.

10. The complex of claim 8, wherein the peptide having at least one immunogenic epitope is a viral oncogenic protein.

11. The complex of claim 8, wherein the peptide having at least one immunogenic epitope is papillomavirus E7 protein.

12. The complex of claim 8, further comprising a linker for linking the chimeric polypeptide.

13. The complex of claim 1, wherein the L2 polypeptides are 100 amino acids in length or less.

14. The complex of claim 1, wherein the L2 polypeptide comprises a site-directed mutation.

15. The complex of claim 1, wherein the L2 polypeptide complex comprises one or more peptides selected from Table 2.

16. The complex of claim 1, wherein the Xaa of the second motif is Tyr, Val, Thr or Glu.

17. A therapeutic vaccine for eliciting an immune response to papillomavirus infection comprising, a therapeutically effective amount of a complex comprising:

a) a first polypeptide comprising a papillomavirus L2 capsid polypeptide or peptide fragment thereof;

b) the first polypeptide further comprising papillomavirus capsid protein L1-interaction sequences(s) comprising a first motif of Pro-$Xaa_{(4)}$ to $Xaa_{(10)}$-Pro followed by a second motif of Phe-Xaa-Leu-His-Pro or Tyr-Xaa-Leu-His-Pro; and c) a second polypeptide comprising five papillomavirus L1 capsid polypeptide or five truncated papillomavirus capsid L1 that form a capsomere non-covalently bound to the first polypeptide the two polypeptides form a complex.

18. The therapeutic treatment of claim 17, wherein one or more of the first polypeptide and second polypeptide is fused at its amino- or carboxy-terminus to a peptide having at least one immunogenic epitope to form a chimeric protein.

19. The complex of claim 17, further comprising a peptide having at least one immunogenic epitope.

20. A complex comprising:

a) a first polypeptide comprising a papillomavirus L2 capsid polypeptide or peptide fragment thereof;

b) the first polypeptide further comprising papillomavirus capsid protein L1-interaction sequences(s) comprising a first motif of Pro-$Xaa_{(4)}$ to $Xaa_{(10)}$-Pro followed by a second motif of Phe-Xaa-Leu-His-Pro or Tyr-Xaa-Leu-His-Pro;

c) wherein the L1 interaction sequence is an amino acid sequence comprising SEQ ID NO:1 comprising [HPV11] identified at amino acid sequence positions 1-455 and d) further comprising a second polypeptide comprising five papillomavirus L1 capsid polypeptide or five truncated papillomavirus capsid L1 that form a capsomere non-covalently bound to the first polypeptide the two polypeptides form a complex.

21. A method to elicit an immune response to papillomavirus in a subject, the method comprising administering to the subject a complex comprising:
   a) a first polypeptide comprising a papillomavirus L2 capsid polypeptide or peptide fragment thereof;
   b) the first polypeptide further comprising papillomavirus capsid protein L1-interaction sequences(s) comprising a first motif of Pro-Xaa$_{(4)}$ to Xaa$_{(10)}$-Pro followed by a second motif of Phe-Xaa-Leu-His-Pro or Tyr-Xaa-Leu-His-Pro; and
   c) a second polypeptide comprising five papillomavirus L1 capsid polypeptide or five truncated papillomavirus capsid L1 that form a capsomere non-covalently bound to the first polypeptide the two polypeptides form a complex.

22. The complex of claim 21, further comprising a peptide having at least one immunogenic epitope.

23. A prophylactic treatment for eliciting an immune response to papillomavirus in a subject comprising, administering to the subject a prophylactically effective amount of a complex comprising:
   a) a first polypeptide comprising a papillomavirus L2 capsid polypeptide or peptide fragment thereof;
   b) the first polypeptide further comprising papillomavirus capsid protein L1-interaction sequences(s) comprising a first motif of Pro-Xaa$_{(4)}$ to Xaa$_{(10)}$-Pro followed by a second motif of Phe-Xaa-Leu-His-Pro or Tyr-Xaa-Leu-His-Pro; and
   c) a second polypeptide comprising five papillomavirus L1 capsid polypeptide or five truncated papillomavirus capsid L1 that form a capsomere non-covalently bound to the first polypeptide the two polypeptides form a complex.

24. The prophylactic treatment of claim 23, wherein one or more of the first polypeptide and second polypeptide is fused at its amino- or carboxy-terminus to a peptide having at least one immunogenic epitope to form a chimeric protein.

25. The complex of claim 23, further comprising a peptide having at least one immunogenic epitope.

26. A method of inducing an immune response against a polypeptide in a subject comprising:
   a) providing a chimeric first polypeptide composition comprising a polypeptide having at least one immunogenic epitope fused to a papillomavirus L2 capsid polypeptide or peptide fragment thereof;
   b) a second polypeptide comprising five papillomavirus L1 capsid polypeptide or five truncated papillomavirus capsid L1 that form a capsomere non-covalently bound to the first polypeptide the two polypeptides form a complex; and
   c) administering the polypeptide complex composition to the subject;
wherein the administration is effective to induce an immune response against the polypeptide.

27. The method of claim 26, wherein the polypeptide is selected from the group consisting of ras, EGFR, BRAC, Her2/neu, myc, abl, P1A, MAGE-1, MAGE-3, MAGE-6, BAGE, GAGE-1/2, GAGE-8, GAGE-6, RAGE-1, GnTV, mucin, connexin-37, ribosomal protein L9, gag IAP, gp70 env MuLV, p53, DEAD box helicase p68, c-akt, MUM-1, CDK4, beta-catenin, HLA-A2, bcr-abl, CASP-8 and KIAA0205 proteins.

28. The method of claim 27, wherein the polypeptide is selected to have the sequence of a mutant form of the ras, EGFR, BRAC, Her2/neu, myc, abl, P1A, MAGE-1, MAGE-3, MAGE-6, BAGE, GAGE-1/2, GAGE-8, GAGE-6, RAGE-1, GnTV, mucin, connexin-37, ribosomal protein L9, gag IAP, gp70 env MuLV, p53, DEAD box helicase p68, c-akt, MUM-1, CDK4, beta-catenin, HLA-A2, bcr-abl, CASP-8 or KIAA0205 proteins.

29. The method of claim 26, wherein the polypeptide is from a viral-associated protein or a tumor antigen.

* * * * *

UNITED STATES PATENT AND TRADEMARK OFFICE
CERTIFICATE OF CORRECTION

| | | |
|---|---|---|
| PATENT NO. | : 8,039,001 B2 | Page 1 of 1 |
| APPLICATION NO. | : 12/418481 | |
| DATED | : October 18, 2011 | |
| INVENTOR(S) | : Robert L. Garcea et al. | |

It is certified that error appears in the above-identified patent and that said Letters Patent is hereby corrected as shown below:

Column 1, line 5
Please add the following paragraph below title in the specification:

This invention was made with government support under grant number CA37667 awarded by the National Institutes of Health. The government has certain rights in the invention.

Signed and Sealed this
Sixth Day of March, 2012

David J. Kappos
*Director of the United States Patent and Trademark Office*